(12) United States Patent
Klauke et al.

(10) Patent No.: US 8,003,372 B2
(45) Date of Patent: Aug. 23, 2011

(54) DEVICE FOR PERFORMING CELL ASSAYS

(75) Inventors: Norbert Klauke, Glasgow (GB);
Jonathan Mark Cooper, Glasgow (GB)

(73) Assignee: The University Court of the University of Glasgow (GB)

( * ) Notice: Subject to any disclaimer, the term of this patent is extended or adjusted under 35 U.S.C. 154(b) by 1396 days.

(21) Appl. No.: 10/503,449

(22) PCT Filed: Feb. 5, 2003

(86) PCT No.: PCT/GB03/00514
§ 371 (c)(1),
(2), (4) Date: Aug. 30, 2005

(87) PCT Pub. No.: WO03/067251
PCT Pub. Date: Aug. 14, 2003

(65) Prior Publication Data
US 2006/0003310 A1    Jan. 5, 2006

(30) Foreign Application Priority Data
Feb. 5, 2002  (GB) .................................. 0202638.3

(51) Int. Cl.
*C12M 1/42*    (2006.01)
(52) U.S. Cl. .................. 435/285.2; 435/287.3
(58) Field of Classification Search .......... None
See application file for complete search history.

(56) References Cited

U.S. PATENT DOCUMENTS

| 4,946,793 A * | 8/1990 | Marshall, III .............. 435/285.2 |
| 5,472,671 A * | 12/1995 | Nilsson et al. ................ 422/102 |
| 5,907,240 A | 5/1999 | Carver, Jr. et al. |
| 6,492,175 B1 * | 12/2002 | Muller et al. ................. 435/450 |

FOREIGN PATENT DOCUMENTS

| WO | WO 93 09838 A | 5/1993 |
| WO | WO 98 54294 A1 | 3/1998 |
| WO | WO 0037628 A1 * | 6/2000 |
| WO | WO 01 25769 A | 4/2001 |
| WO | WO 01 25769 A | 12/2001 |
| WO | WO 02 08748 A2 | 1/2002 |

OTHER PUBLICATIONS

Hong Xing, Hung-Cuong Tran, Thomas E. Knapp, Paul A. Negulescu, and Brian A. Pollok, *A Fluorescent Reporter Assay for the Detection of Ligands Acting Through G1 Protein-Coupled Receptors*, Journal of Receptor and Signal Transduction Research, vol. 20(No. 4), (2000), 189-210.

* cited by examiner

*Primary Examiner* — Jim Ketter
(74) *Attorney, Agent, or Firm* — Joseph T. Leone, Esq.; DeWitt Ross & Stevens S.C.

(57) ABSTRACT

A device for performing cell assays has at least one assay site. The site comprises a pair of stimulating electrodes and a cell confinement cavity for confining at least one cell in an extracellular fluid medium. The cell confinement cavity and the stimulating electrodes are arranged so that, in use, each cell is exposable to an electrical field generated by a potential difference applied across the stimulating electrodes. The stimulating electrodes are spaced a distance apart such that the potential difference can induce field stimulation of each cell and simultaneously be below the level that would result in electrolysis of the extracellular fluid medium.

18 Claims, 16 Drawing Sheets

DEVICE FOR PERFORMING CELL ASSAYS

FIELD OF THE INVENTION

The present invention relates to a device for performing cell assays, particularly assays involving electrical cell stimulation.

BACKGROUND OF THE INVENTION

Genomics and, more recently, proteomics, have become major industrial activities, often associated with high density, microarray device formats which enable numerous parallel assays.

There has been significantly less activity, however, relating to microassay formats for testing or screening biological cells, e.g. where the functionality of an expressed protein or the activity of a new drug can be studied. A potential advantage of such formats, were they to be more universally adopted, could be a reduction in the high attrition rates in the discovery of pharmaceutical compounds during pre-clinical or clinical trials.

However, conventional cell-based assay devices are relatively limited in terms of the types (or functionalities) of tests that can be performed on cells.

For example, Aurora Biosciences™ have developed a high-throughput GPCR assay in a 3456-well microplate using a human T-cell line (Hong Xing, Hung-Cuong Tran, Thomas E. Knapp, Paul A. Negulescu, and Brian A. Pollok, *A Fluorescent Reporter Assay for the Detection of Ligands Acting Through G1 Protein-Coupled Receptors*, Journal of Receptor and Signal Transduction Research, Vol. 20(No. 4), (2000), 189-210).

Molecular Devices™ have developed FLIPR™ assays which can be used to measure the changes in intracellular calcium ion concentration and membrane potential from cells contained in either 96- or 384-well plates.

WO 01/25769 describes a substrate for determining and/or monitoring electrophysiological properties of ion channels. The substrate makes use of the so-called "patch-clamp" or "voltage-clamp" technique in which a seal is formed at a portion of an ion-channel-containing cell membrane in order to electrically isolate a measuring electrode at the seal from a reference electrode. The measuring electrode can then measure the electrical potential at the sealed-off portion of the cell membrane. This enables the study of e.g. ion channel responses to drugs.

The substrate described in WO 01/25769 has a plurality of sites, each of which has a measuring electrode associated therewith, and one or more reference electrodes. The electrodes described act solely as sensors, for electrochemical (impedance) measurements. The sites are in the form of wells having piping which applies suction to cells placed in the wells, thereby positioning the cells in the wells and forming seals to the cell membranes.

There has however been relatively little development of cellular assay techniques for studying electrically active cells such as myocytes, mast cells or neurons. Such cells are closely associated with major disease states including infarction and neurological disorders like Parkinson's disease. For example, WO 98/54294 describes an apparatus in which an array of microelectrodes are disposed in a cell culture chamber so that detection and monitoring of a voltage signal applied across each electrode can provide information on the electrical characteristics of individual cells. The geometry of electrodes in WO 98/54294 is designed such that they evoke an action potential through an injection of current, although there must be a good electrical contact between the cell and the electrode surface. In addition, impedance measurements made in WO 98/54294 require there to be an electrical contact between the cell and the sensing electrodes.

WO 02/08748 proposes a further substrate for manipulating membrane potentials of living cells via electrical stimulation. This substrate is based on a multiwell plate. An array of electrodes is dipped into the wells, so that an electrode pair is introduced into each well. An aim is to electrically stimulate cells held in the wells while performing optical analysis of transmembrane potential changes.

A drawback, however, of the substrate disclosed in WO 02/08748 is that the electrical fields needed to induce cell stimulation can lead to electrolysis of the well solution. Electrolysis results in bubble formation and a consequent change in chemistry (e.g. pH) of the solution. This in turn can affect the electrical response and indeed the viability of the cells (e.g. due to electroporation).

To limit the extent of electrolysis, WO 02/08748 proposes stimulation protocols which are only up to about one minute in duration. Also the electrical pulses which form the stimulation protocols are kept short, and polarities are inverted to balance charge.

SUMMARY OF THE INVENTION

It is an object of the present invention to provide a device for performing cell assays which may be used to perform high throughput assay screening, and/or which enables a wide range of functional cellular assays to be employed, particularly those involving electrical stimulation of the cells.

A first aspect of the present invention provides a device for performing cell assays, which device has at least one assay site, the site comprising a pair of stimulating electrodes and a cell confinement cavity for confining at least one cell in an extracellular fluid medium, the cell confinement cavity and the stimulating electrodes being arranged so that, in use, the or each cell is exposable to an electrical field generated by a potential difference applied across the stimulating electrodes, wherein the stimulating electrodes are spaced a distance apart such that the potential difference can induce field stimulation of the or each cell and simultaneously be below the level that would result in electrolysis of the extracellular fluid medium. For example, the stimulating electrodes may be no more than 1 mm, or 400, 200, 100 or 50 μm apart.

The present inventors have realised that by reducing the distance between the stimulating electrodes the potential required to produce a given field is decreased, and hence the problems of electrolysis in the extracellular fluid medium can be avoided or significantly reduced. Compared with WO 02/08748, this enables significantly longer term stimulation protocols to be adopted, e.g. greater than one minute and in some instances up to 24 hours in duration.

In an aqueous medium, $H^+$ can be generated at an anode at a potential of more than about 1.0 V relative to an Ag/AgCl reference electrode, whilst $OH^-$ can be generated at a cathode at a potential of more than about 0.83 V relative to such a reference electrode. At higher potentials $H_2$ and $O_2$ may also be generated forming bubbles, and indeed WO 02/08748 describes changes in pH and bubbles formation. However, the present inventors have found that by miniaturising the stimulating electrodes and reducing the distance between them, a sufficiently high field strength can be generated to initiate stimulation of the cell, e.g. by hyper-, or de-polarisation, while simultaneously maintaining a voltage across the electrodes below the level that would initiate the generation of electrolytic products (e.g. $H^+$, $OH^-$, $O_2$ or $H_2$) through electrolysis.

The avoidance of bubble formation is particularly important in a device which incorporates microfluidics features (discussed below), as bubbles can block the flow of fluid along flow channels.

The threshold field strength required for activation of ventricular myocytes is about 40 V/cm. For other cell types the threshold field strength may be different. The threshold field strength is also a function of the physiological state of the cell (e.g. after pharmaceutical challenge the field strength required to initiate depolarisation may be increased or decreased). Preferred embodiments of the present invention bring the stimulating electrodes as close to the cell as possible, but without actually contacting the cell surface.

In one embodiment a field strength of 40 V/cm can be generated by applying a potential difference of 0.8 V across a pair of stimulating electrodes which are 200 microns apart. In such a circumstance, the voltage can be maintained below the level for the production of electrolytic products. A myocyte (typical length 100-150 microns) can therefore be positioned parallel to the electric field lines, between the stimulating electrodes, and depolarisation can be promoted by field stimulation. For other cell types which require a different field strength for polarisation, the electrode geometry can be adjusted accordingly.

Preferably, the cell confinement cavity and the stimulating electrodes are arranged so that, in use, the or each confined cell (and preferably substantially the entirety of the or each confined cell) is exposable to a region of substantially uniform electrical field generated by the stimulating electrodes.

Thus a substantial part, and preferably the whole, of the cell can be stimulated by the uniform electrical field. This is in contrast to examples described in WO 02/08748 in which fields applied to cells are not uniform. It is also in contrast to the patch-clamp approach, which looks at the behaviour of ion channels enclosed within the relatively small patch area of the cell under investigation.

Preferably, in use, the or each confined cell does not contact the stimulating electrodes. This provides a contrast with the patch- or voltage-clamp approach (or other methods for current injection, e.g. WO 98/54294) in which the cell or cells are in contact with or impaled by an electrode.

Electrical field stimulation relies on the ability of excitable cells to generate an action potential in response to a depolarisation of the membrane potential above an excitation threshold. When a cell is in contact with, or impaled upon an electrode (e.g. during patch- or voltage-clamping), typically an input impedance of about 1 MΩ is produced, and a cardiomyocyte cell will require an-injection current of about 1 nA to cause a membrane depolarisation of about 10 mV, and thereby generate an action potential. In similar circumstances other electrically active cell types may require injection currents of between 1-10 nA to cause depolarisation. We have found, however, that cell polarisation of electrically excitable cells (including electrically active cells such as cardiomyocyctes) can be achieved without contact or impalement upon an electrode, allowing longer term recording of signals from cells. Such polarisation can be achieved by means of e.g. high extracellular potassium (preferably at least 50 or 100 mM $K^+$) or field stimulation, or a combination thereof.

In the context of the invention, the stimulating electrodes are preferably integrated into the cell confinement cavity. Such electrodes can be used to cause depolarisation. This can enable electrical stimulation of individual cells in ultralow (pL-nL scale) volumes. In use, one electrode of the electrode pair (the anode) has a positive potential with respect to the other (the cathode). The polarity of the stimulating electrodes may be changed (reversed relative to each other, or increased or decreased) during the course of an experiment.

The stimulating electrodes can therefore be used to promote electrical or electro-physiological activity (e.g. through the depolarisation or hyper-polarisation of the cell membrane in electrically active cells). Such electrical conditions may occur under physiological conditions or in the presence of known or unknown drugs. Additionally or alternatively, the stimulating electrodes can be used to (i) electroporate the cell and allow the introduction of particles, molecules or ions, and/or (ii) to enable electro-fusion to combine cells. Thus field stimulation, electroporation and electro-fusion can be performed sequentially or simultaneously.

Non-electrically active cells can be transformed into electrically excitable cells by transfecting them with voltage sensitive ion specific channels. These heterologous expressed voltage sensitive ions channels open upon membrane depolarisation or hyper-polarisation, thus creating sufficient current flow which can be monitored either fluorescently, electronically or electrochemically. Such cells would have broad applicability to the device of the present invention.

At the same time the cell's metabolic response during the period of activation can be monitored in situ by means of chemical, optical or electrochemical analysis of the cellular byproducts. Such monitoring may occur under physiological conditions or in the presence of known or unknown drugs.

For example, it is possible to implement a protocol in which a cell or cells are field stimulated by the pair of stimulating electrodes, whilst the cell is bathed in a fluorophore, which reports on the membrane potential. The opening and closing of the ion channels in the cell or cells can then be monitored optically, by measuring a change in the signal from the fluorophore. This may be measured directly, or as "flicker noise". Other methods may involve the measurement of an electrical or electrochemical signal at one or both of the stimulating electrodes. For example, either or both of the current flow or the applied threshold potential (at a stimulating electrode) required to cause the cell to depolarise or hyper-polarise, and thus generate an action potential, may be measured, e.g. under physiological conditions or in the presence of a known or unknown drug. Such a measurement would report on the electro-physiological state of the cell.

Tests which make use of such cell stimulation modes may be termed "active" cell assays, as stimulation can influence the cell during assay measurements. This is in contrast to conventional patch-clamp approaches in which little or no attempt is made to influence the cell or cells and which can therefore be termed "passive" cell assays.

For example, the device of the present invention may be used to perform assays in which the amount or location of $Ca^{2+}$ in or around the cell is measured or monitored, e.g. by means of $Ca^{2+}$-sensitive fluorophores, before, during or after electrical stimulation.

However, other chemical, optical, electrochemical, electromagnetic etc. methods of measuring cellular activity known to the skilled person may be used to perform assays using the device.

Preferably, by a "substantially uniform electrical field", we mean-that the electrical field strength varies transversely to the electrical field lines by no more than 10%, and more preferably no more than 5, 2, 1 or 0.5%. Typically the field lines in the region of substantially uniform electrical field are substantially straight.

Preferably the region of substantially uniform electrical field extends along and/or transversely to the direction of the field lines for a distance of at least 2 μm, and more preferably at least 5, 10, 20, 30, 50, 80, 100, 150, 200 or 400 μm, or 1 mm. Typically the region is bounded at one side by the floor of the cell confinement cavity. The larger the size of the region, the more cells can be confined in the confinement cavity and exposed to substantially the same electrical field.

In one embodiment, the region of substantially uniform electrical field occupies a volume of at least 1 pL (and preferably at least 5, 10, 50 or 100 pL). However, the region may occupy at least 500 pL, or 1, 2, 3, 5 or 10 nL. In general, larger volumes are preferred when, in use, the fluid in the cell confinement cavity is renewed (e.g. by a pipette or a dispenser or a flow channel—as discussed in more detail below) during an assay such that a higher degree of convective fluid movement, and hence cell movement, in the cavity can be expected. The larger volumes then help to ensure uninterrupted exposure of the cell or cells to the region of substantially uniform electrical field.

However, it may also be of physiological interest to produce a region of substantially uniform electrical field which is smaller than the cell under investigation e.g. to promote a local-depolarisation or hyper-polarisation on part of the cell. The propagation of that depolarisation or hyper-polarisation across the cell can then be studied under physiological conditions, or after the addition of a known or unknown pharmaceutical compound. In such a case it is particularly preferable if the stimulating electrodes are not in contact with the cell. Preferably also the electrodes are smaller than the cell.

In one embodiment, the stimulating electrodes extend (preferably substantially parallel to each other) at opposing sides of the cell confinement cavity in the direction perpendicular to the floor of the cell confinement cavity. This serves to increase the extent/volume of the region of substantially uniform electrical field. If the floor of the cell confinement cavity defines an x-y plane, the electrodes can be said to extend in the z-direction. The stimulating electrodes may extend in the direction perpendicular to the floor of the cavity for a distance of at least 2 μm (and preferably at least 5, 10, 20, 30, 40, 50 or 80 μm). Preferably the electrodes extend from the floor of the cell confinement cavity.

The stimulating electrodes may be formed by electroplating from solution e.g. a noble metal such as gold, iridium or platinum or an alloy mixture of two or more thereof. In one embodiment, substantially planar "precursor" electrodes (which may be printed or otherwise conventionally formed on the floor of the confinement cavity) are provided at opposing sides of the cell. Electroplating is then used to thicken the precursor electrodes in the out-of-plane direction (which is typically perpendicular to the cavity floor) to form the stimulating electrodes, whereby the thickness of the region of the substantially uniform electric field is increased.

It is desirable to form a surface layer on either or both of the stimulating electrodes to reduce the polarisation due to the electrical double layer adjacent the electrode surface when fluid is contained in the cavity. This helps to avoid or reduce capacitive discharges when current starts to flow between the electrodes.

An electrode surface layer may also be used to reduce a possible tendency for such fluid to decompose or denature under the influence of the electrical field. For example, the stimulating electrodes may be coated by a modifying ad-layer, which reduces the overpotential for the hydrolysis of water, thus enabling a higher voltage to be applied across the electrodes without initiating electrolysis.

The assay site may further comprise one or more sensor electrodes. Typically the sensor electrodes measure responses in the or each cell exposed to the region of substantially uniform electrical field generated by the stimulating electrodes. In use, the sensor electrodes are either contacted to the surface of the cell (in which case they may be termed impedance electrodes), or they are not in contact (in which case they may be termed biosensor electrodes). The sensor electrodes may be integrated into the assay site. If the device is fabricated using stacked photolithographic layers, electrodes formed on different photolithographic layers may be separated by dielectric layers (e.g. chemical vapour deposited (CVD) silicon nitride or polyimide).

For example, field stimulation, electroporation or electrofusion may cause a change in the capacitance of the cellular envelope or in the surface to volume ratio of the or each cell. This can be monitored by impedance measurements obtained by contacting the sensor electrodes to the cell surface.

However, the sensor electrodes may be used to monitor more generally the electrochemistry of the cell (including biosensor applications). For example, it is possible to couple enzyme catalysed reactions to an electrochemical detection protocol (e.g. a sensor electrode can function as an amperometric or a potentiometric sensor) and monitor metabolites such as lactate and glucose, glutamate, NAD+, NADH, during the course of field stimulation. Thus the enzyme lactate oxidase (which in the presence of lactate and oxygen, or another electron acceptor, will produce the electro-active compound hydrogen peroxide) may be introduced into the confinement cavity, thereby making it possible to monitor the metabolic activity of the cell through the detection of hydrogen peroxide which is directly related to the production of cellular lactate. Similarly, other metabolites can be monitoring using enzyme linked reactions known to those skilled in the art. In a further example, ions, such as $K^+$, $Na^+$ and $Ca^{2+}$, may be measured electrochemically using an ion selective sensor electrode as a potentiometric sensor.

Less desirably, either or both of the stimulating electrodes can be used for monitoring cellular impedance, although in such a case the cell would need to be in contact with the electrode, and stimulation/electroporation/electrofusion could not be performed at the same time as sensor measurement. In such a case preferably the surface of the electrodes is modified by electrodeposition of conducting polymer (e.g. polypyrrole) or nonconducting polymer (e.g. polyphenole) or by addition of ad-layers, such as thiols or proteins, to improve the analytical response.

In one embodiment the chargeable surface area of the stimulating electrodes is enlarged (and hence the current through the electrode is increased for a given applied voltage) by coating the electrodes with a chargeable surface area enhancing agent, such as a conductive polypyrrole polymer or platinum black.

Furthermore, the present inventors have recognised that the amount of current entering a cell during an applied voltage pulse is related to the extracellular space in the confinement cavity. The lower the available extracellular space, the more charge passes through the cell membrane (for a given applied voltage) thus contributing to the membrane potential change which causes either de- or hyperpolarisation, depending on the nature and orientation of the cell with respect to either the cathode or the anode.

Thus preferably, the extracellular space within the cell confinement cavity is less than 20 times (and more preferably less than 10, 5 or 2 times) the total volume of the cell or cells intended to be confined within the cavity. For example, a cell confinement cavity intended to confine a cardiomyocyte of about 36 pL volume may have a volume of up to about 400 pL.

Reducing the extracellular space within the cell confinement cavity decreases the dilution of measurands therein and thus provides analytical advantages in the measurement of extracellular metabolites and ions (using electrochemical or optical methods, or other techniques known to those skilled in the art).

Typically the cell confinement cavity takes the form of a well, the top of which, in use, is closed with a dielectric layer which may be a layer of mineral oil, a polymer, a membrane or semi-permeable membrane or any other physical barrier. Closing the well in this way effectively limits the amount of extracellular space, and also serves to reduce evaporation.

The cavity may contain a plurality of cells so that cells can be stimulated and assayed in parallel to increase the assay throughput. For example, at least 2, 5 or 20 cells may be in the or each cavity, but preferably at least 100 or 200 cells to provide good biological representation. When assays are performed on multicellular preparations, it is preferred that the confinement volume is as low as possible consistent with enabling physiological functioning.

Typical cell sizes are of the order of 5 to 200 μm. Thus the cell confinement cavity may occupy a volume of less than 500 pL (and preferably less than 200, 100, 50 or 10 pL) and/or the smallest dimension of the cell confinement cavity may be less than 200 μm (and preferably less than 100, 50, 20 10, or 5 μm). Such sizes for the cavity are suitable for performing assays on single cells. However, particularly when it is intended to confine a plurality of cells in the cavity or when, in use, the fluid in the cell confinement cavity is renewed, the cavity may occupy a volume of less than 100 nL (but preferably less than 50, 10, 5, 3, 2 or 1 nL)

The confinement cavity may be shaped to encourage the or each cell to adopt a predetermined position in and/or orientation with respect to the region of substantially uniform electrical field. For example an elongate cuboid confinement cavity would be a preferred shape to orient a correspondingly elongate heart cell. In particular, if the stimulating electrodes are at respective ends of the elongate cross section, the heart cell can be orientated such that it lies parallel to the stimulating electrical field.

Preferably the device comprises a plurality of assay sites. This allows multiple parallel assays to be performed. For example, a multiple assay device may comprise at least 2 sites, and preferably at least 5, 10, 50, 100, 500, 1000 or 5000 sites.

In a preferred embodiment, the device comprises at least one flow channel in fluid communication with the confinement cavity of the or each assay site, whereby a flow of fluid through the cavity can be produced. This allows nutrients to be supplied to and/or waste products to be removed from the cavity, thus promoting or maintaining cell viability. The flow channel may also be used to withdraw (e.g. extracellular) fluid from the cavity for testing. Furthermore, the flow channel can be used to transport a test cell or cells to the cavity.

Additionally or alternatively, the device may comprise one or more (preferably two or three) substance delivery channels per assay site to add substances to the cell confinement cavity. The channels may be used in an active cell assay to apply locally a drug or drugs, whereby the immediate impact of the drug or drugs on the metabolic response of an electrically stimulated cell or cells can be measured. The typically small extracellular volume in the cavity enables switching in the millisecond time range, as may be required.

Preferably, when there are a plurality of delivery channels, the delivery channels open to the cell confinement cavity from different directions. Thus different areas of the cell or each cell can be exposed to different drug concentrations separated, for example, by laminar flows.

The proper functioning of such flow channels and delivery channels is enhanced by the avoidance or reduction of electrolysis in the extracellular fluid medium (achieved in the manner described above). This is because bubbles formed by electrolysis can block flow through the channels.

Indeed a second aspect of the present invention provides a device for performing cell assays, which device has at least one assay site, the site comprising a pair of stimulating electrodes and a cell confinement cavity for confining at least one cell, the cell confinement cavity and the stimulating electrodes being arranged so that, in use, the or each cell is exposable to an electrical field generated by the stimulating electrodes, wherein the device further comprises at least one flow channel which is in fluid communication with the confinement-cavity.

A third aspect of the present invention provides a device for performing cell assays, which device has at least one assay site, the site comprising a pair of stimulating electrodes and a cell confinement cavity for confining at least one cell, wherein the cell confinement cavity and the stimulating electrodes are arranged so that, in use, the or each confined cell (and preferably substantially the entirety of the or each confined cell) is exposable to a region of substantially uniform electrical field generated by the stimulating electrodes.

In relation to the second and third aspects, it is preferred, but not essential, that the stimulating electrodes are spaced a distance apart such that the potential difference, which, in use, is applied across the stimulating electrodes to generate the electrical field, can induce field stimulation of the or each cell and simultaneously be below the level that would result in electrolysis of the extracellular fluid medium.

Any one or any combination of the optional features of the first aspect may be applied to the second and third aspects.

A further aspect of the present invention provides a device for performing cell assays according to one of the previous aspects, in which the cell confinement cavity confines at least one cell (and preferably a plurality of cells) and/or a fluid medium.

A further aspect of the present invention provides for the use of the device of any one of the previous aspects for performing a cell assay.

A cell assay may be defined as a test which examines or determines the effect of an agent on a cellular response. The agent could be a drug, a peptide, a protein or glycoprotein, a sugar or carbohydrate, a ligand, a polymer, a bead, a chemical, another cell, a virus, a microbe, a nucleic acid or a polynucleotide. The cellular response could be, but is not confined to, the following: cell-surface receptor or ion channel signaling, intracellular ion fluxes, intracellular molecular movement, signal transduction, gene expression, changes in subcellular organelle activity, cell morphology, pinocytosis, internalisation, secretion, alteration in cell-cell interfaces, apoptosis, necrosis, or cell death.

A further aspect of the present invention provides for the use of the device of any one of the previous aspects for electrical field stimulating one or more cells, electroporating one or more cells, or electro-fusing two or more cells.

BRIEF DESCRIPTION OF THE DRAWINGS

Specific embodiments of the present invention will now be described with reference to the following drawings in which.

DETAILED DESCRIPTION OF THE INVENTION

The present invention relates to an active cell-based assay system, which can be used to alter the electrical properties or promote physical change within a cell.

In the former case, a process known as field stimulation (resulting from the application of a voltage across the cell, or more specifically across one or more regions of the cell membrane) alters the electrical properties of the cell so that the cell responds according to the size and nature of the electrical stimulation. The response has been shown (Cheng, David Ker-Liang, Leslie Tung and Eric A. Sobie, *Nonuniform responses of transmembrane potential during electric field stimulation of single cardiac cells*, Am. J. Physiol., 277, (1999), H351-H362) to result from differential activity of membrane proteins involved in ion transport. Different ions may then move into or out of the cell resulting in either an electro-physiological responses (such as the beating of a myocyte, or an action potential of a neuron), or receptors in the cell membrane may then become stimulated.

In the latter case, when the application of a field across the membrane causes a physical (but not necessarily permanent) change in the cell, two examples may be cited. In the first, two cells can be encouraged to fuse. In the second, the permeability of the cell membrane can be changed (by a process known as electroporation) so that it becomes possible for particles, molecules or ions to be introduced into the cell via the cell membrane or artifacts therein.

In following examples, we describe the fabrication of devices for performing cell assays according to the present invention, and uses of the devices for performing tests on cells.

EXAMPLE 1

Device Fabrication

Positive photoresist (product name S1818) was photolithographically patterned on a microscope glass coverslip (22×64 mm, thickness No. 1, 0.13-0.17 mm) using electron-beam written chromic masks. A layer of titanium (10 nm) and a second layer of gold (100 nm) were evaporated on top of the patterned glass surface. Subsequent removal of the Ti/Au covered layer of the positive photoresist left behind on the glass 20 μm wide Ti/Au parallel line precursor electrodes 200 μm apart from each other and each line having at one end a bonding pad.

Figure 1:
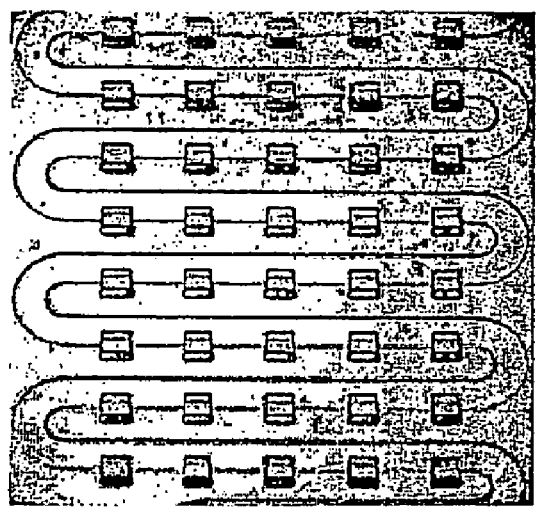
FIG. 1a shows a SU-8 master mold used to form a polymeric (e.g. PDMS) sheet shown schematically in FIG. 1b, FIG. 1b also showing schematically a coverslip with electrode lines which are aligned with through-holes in the PDMS sheet, FIGS. 2a and b respectively show actual top and schematic side views of an assembled device.
Figure 1:
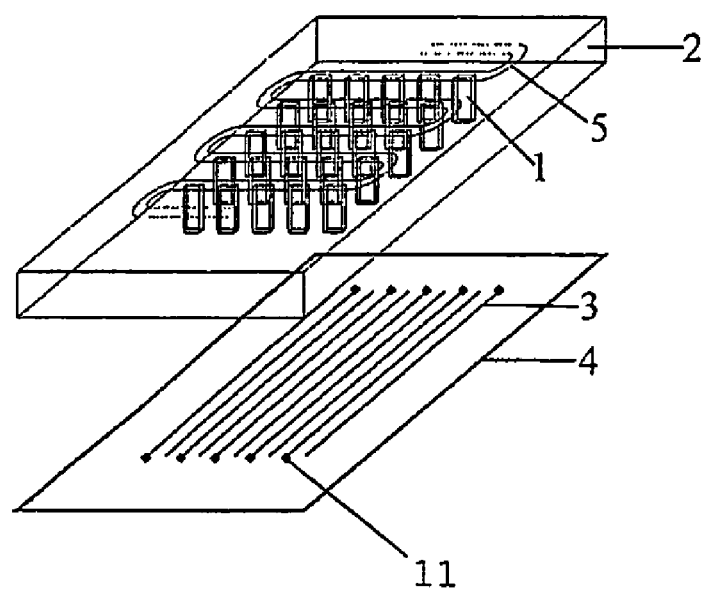
Figure 2:
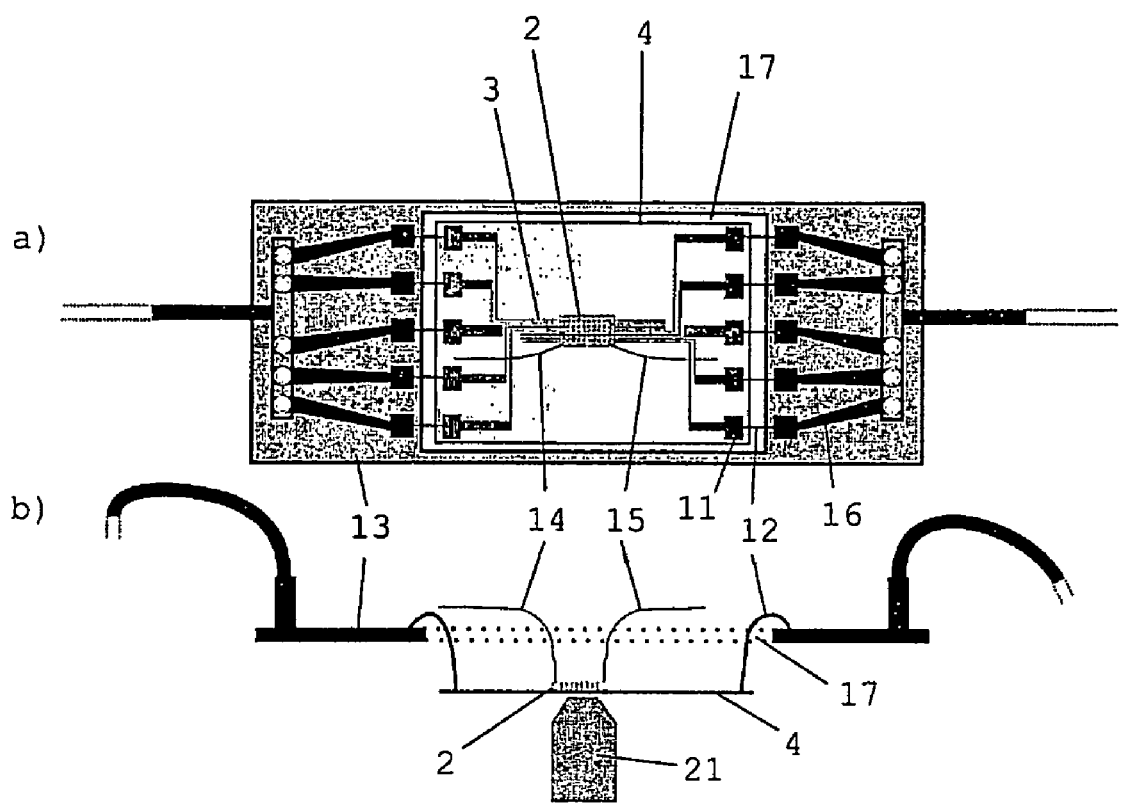

FIG. 1b shows schematically the microscope glass coverslip 4 with electrode lines 3 and bonding pads 11, and FIGS. 2a and b respectively show schematic top and side views of an assembled device which incorporates the coverslip of FIG. 1b.

The bonding pads 11 were connected with 200 μm thick gold wire 12 to the copper electrodes 16 of a printed circuit board (PCB) 13 with a central rectangular window 17 to allow the transmission of light to excite fluorochromes or transilluminate cells.

A 200-400 μm thick rectangular sheet of polydimethylsiloxane (PDMS), sized to cover a central area of the patterned glass coverslip, was molded using a master mold (shown in FIG. 1a). The master was microfabricated in SU-8, a high aspect ratio negative photoresist. The molding process produced a rectangular array of square cross-section, cylindrical through-holes in the PDMS sheet, each through-hole corresponding to one assay site. A serpentine flow channel was also formed by the molding process on one side of the sheet to connect the wells in series.

As shown in FIG. 1b, the lines of through-holes 1 in the PDMS sheet 2 were aligned with respective pairs of adjacent electrode lines 3 on the coverslip 4, with the flow channel 5 on the outer face of the PDMS sheet. Flexible tubing 14, 15 was connected to respectively the inlet and outlet of the flow channel 5. A syringe (not shown) connected to tubing 15 allowed a negative pressure to be applied to draw fluid from a reservoir (not shown) via tubing 14 and into the wells.

The PDMS sheet was then hermetically sealed to the coverslip to form a cell assay device, one end of each through-hole being closed off to form a 200-400 μm deep well (i.e. a cell confinement cavity) with a pair of precursor electrodes at the glass floor of the well.

Figure 3:
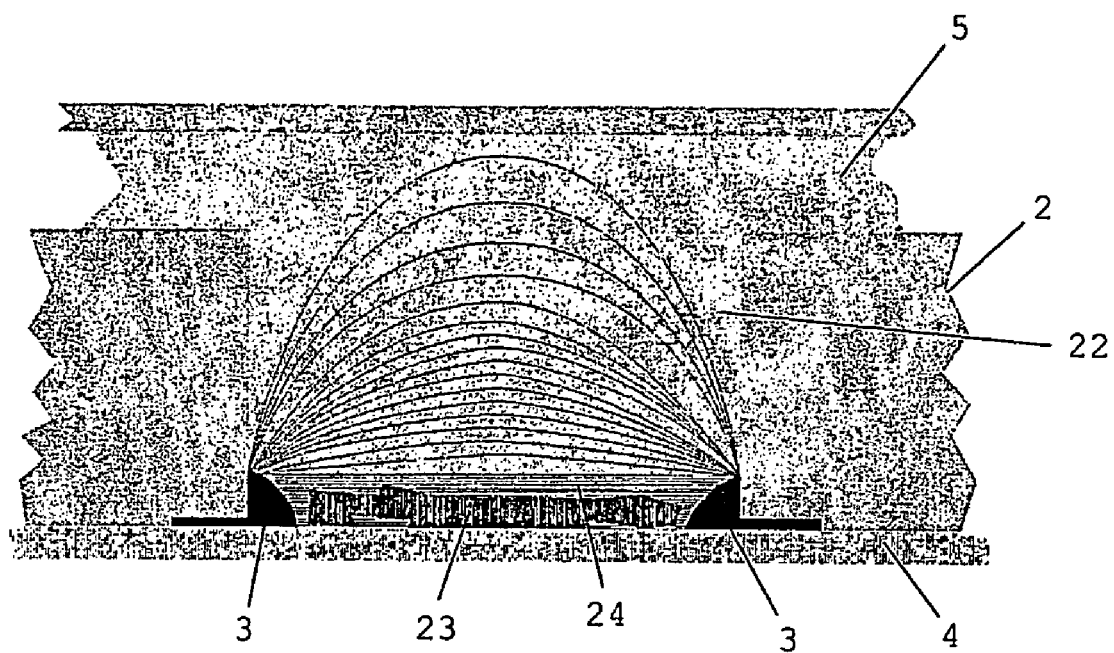
FIG. 3 shows a schematic cross section through a cell confinement cavity of the device of FIGS. 2a and b.

The precursor electrodes were post-processed by electroplating to produce 10-20 μm thick stimulating electrodes. This was accomplished by electroplating from a solution (drawn into each well via tubing 14, 15 and flow channel 5) onto the 100 nm thick gold layers with either gold, iridium or platinum. As a result, the respective electroplated stimulating electrodes extended 10-20 μm high up the sides of each well as shown in FIG. 3, which is a schematic cross section through one well 22 containing a cell 23. The electroplating thus provided an additional seal against leakage of fluid into or out of well at the boundary between the coverslip and the PDMS sheet.

Furthermore, as shown in FIG. 3, a region of substantially uniform electrical field with electrical field lines 24 running parallel to the surface of the coverslip can be produced between adjacent electrode pairs, the region extending approximately from the floor of the well to the top of the stimulating electrodes. In use, therefore, a cell can be completely confined in this region and exposed to the uniform electrical field.

Optional post-processing was then performed on the electroplated stimulating electrodes to deposit a (conducting or insulating) polymer or a dielectric coating by CVD or other deposition method. This changed the polarisation characteristics of the electrode, and thereby reduced the risk that cellular processes would be damaged or altered by large voltage drops or high currents, passing through the cell.

To enlarge the chargeable area, and thus reduce the potential for hydrolysis, the electrode surface was further coated either with the conducting polymer polypyrrole or with silicon nitride or platinum black.

Isolation of Cardiomyocytes

Single cardiac myocytes were isolated from rabbit ventricles by collagenase digestion (D. A. Eisner, C. G. Nichols, S. C. O'Neill, G. L. Smith and M. Valdeomillos, *The effects of metabolic inhibition on intracellular calcium an pH in isolated rat ventricular cells*, Journal of Physiology, 411, (1989), 393-418) and kept in Base Krebs Solution, containing 120 mM NaCl, 20 mM sodium N-hydroxyethylpiperazine-N'-2-ethane sulphonic acid, 5.4 mM KCl, 0.52 mM $NaH_2PO_4$, 3.5 mM $MgCl_2.6H_2O$, 20 mM Taurine, 10 mM Creatine, 100 mM Glucose, 0.1% BSA, 0.1 mM $CaCl_2$. The pH was adjusted to 7.4 with 100 mM NaOH.

Single cells were selected with a sucking capillary and placed either directly into respective empty wells of the cell assay device or were sucked into the flow channel 5 (via tubing 14) until they reached the respective wells. Each cell was then allowed to sediment to the glass floor. The 200-400 μm depth of the wells was sufficient to prevent the myocytes from washing out of the wells while fluid movement through the flow channel washed out cellular byproducts released from the cells during electrical stimulation. Evaporated or absorbed fluid inside the well could also be replaced via the flow channel.

Figure 4:
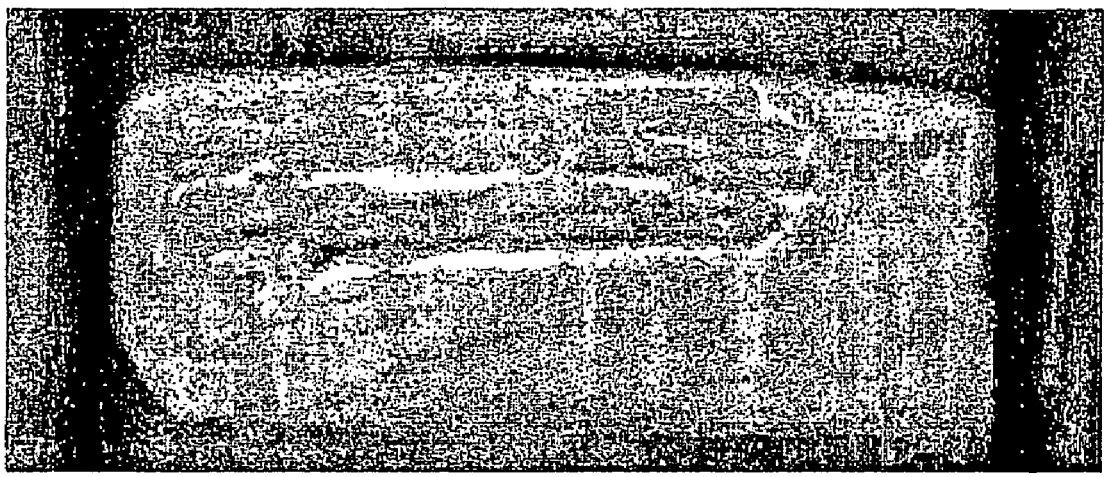
FIG. 4 shows a myocyte, viewed through a microscope, in a well formed by one of the through-holes in the PDMS sheet of FIG. 1b.

The wells containing cells were subsequently viewed with a high numerical aperture x40 oil immersion lens 21 (shown in FIG. 2) and fluorescence microscope in order to relate calcium flux (as evidenced by changes in the emission of calcium-sensitive dye) and cell stimulation (as evidenced by cell shortening). These techniques are described in more detail below. FIG. 4 shows a myocyte in one of the wells.

Evaluation of Calcium Flux

The calcium-sensitive dye fura-2 was introduced into the cardiomyocytes as membrane permeable ester derivative (acetoxymethylester). Once inside a cell the lipophilic residue is cleaved through intracellular esterases to activate the fluorochrome.

The intracellular fluorochrome was excited at 340 and 380 nm every 100 ms using a monochromator (TILL Photonics™) mounted on a Zeiss Axioscope™ upright fluorescence microscope. The emission was passed through a 470 nm dichroic mirror and a 510 nm glass filter to the CCD chip of a cooled CCD camera. The intensity of the excitation light was adjusted by a neutral density filter (OD=2). The emission was evaluated at both wavelengths at different regions inside the cell (cytoplasm, nucleoplasm) and the intracellular concentration of Calcium ($[Ca^{2+}]_i$) was displayed as the 340/380 ratio.

Spatial information about the $[Ca^{2+}]_i$ in electrical field stimulated and spontaneous beating heart cells was detected on color-coded 340/380 ratio images. The extracellular pH sensitive dye fluorescein was excited at 490 nm every 10 ms (line scan) and the emission was passed through a 510 nm dichroic mirror and a 520 nm barrier filter to the camera.

Evaluation of Cell Length

The isolated cardiomyocytes were illuminated with IR-light and electrical field stimulated contractions were recorded to the hard disk of a PC with the b/w CCD camera (12 bit, 10 frames/s). Changes in cell length were measured on the digital movies as changes of the long axis of the cell and plotted against time. To define the cells outline, the grey valued frames of a given sequence were binarised to make the extracellular space black and the intracellular space white. For comparison, the moving edge of a contracting cell was manually marked and the changing distance between the marker at the cell end and the marker at the cell centre was measured automatically.

Cell Stimulation

Initially unipolar pulses of varying strength (20-300 V/cm) and 6 ms duration were delivered with varying frequency (0.5-2.0 Hz) to the stimulating electrodes. The pulse generator (Digitimer™) was triggered by a function generator and the current on the stimulating electrodes was recorded to relate the threshold for excitation of the cell contraction to the geometry and surface of the microelectrodes as well as to the orientation of the cell in the electric field. To repolarize the electrodes a stimulating protocol comprising symmetric bipolar pulses of comparable strength and duration was delivered by means of a home made pulse generator to excite the cells.

Results

The stimulating electrodes were used either for direct field stimulation (pacing), as evidenced by visualisation of cell length, or were used to electroporate the sarcolemma to allow the leakage of $Ca^{2+}$ into the cell. Electroporation evoked spontaneous waves of contraction accompanied by waves of high $[Ca^{2+}]_i$ travelling back and forth along the cell length.

Figure 5:
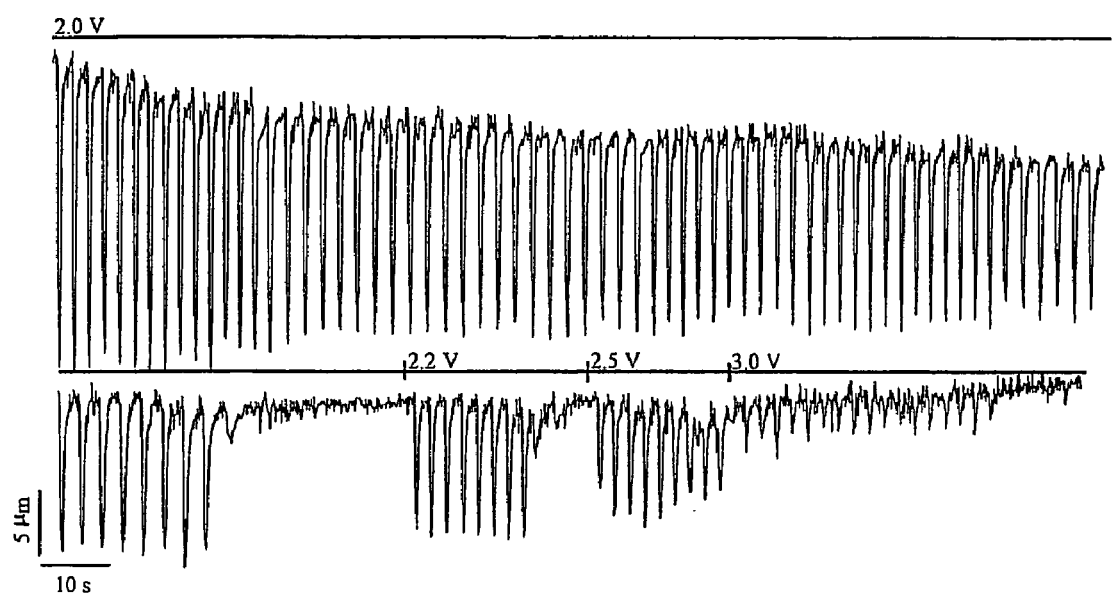
FIG. 5 shows the time course of the contractions of a paced myocyte in an isolated microdroplet.

FIG. 5 shows the time course of contractions of a paced myocyte in an isolated microdroplet (i.e. a microdroplet which was not refreshed by the flow channel). The sudden beat stop after about 3 minutes was due to extracellular pH drop induced by the hydrolysis of water at the surface of (in this case uncoated) stimulating electrodes. Subsequently the potential between the electrodes was raised from 2.0 to 2.2, 2.5 and then 3.0 V, but each increase only evoked a few further beats of decaying amplitude. This demonstrates the importance of maintaining a constant extracellular pH, for when the cell is bathed in an acid solution, its electrical excitability is greatly reduced.

Figure 6:
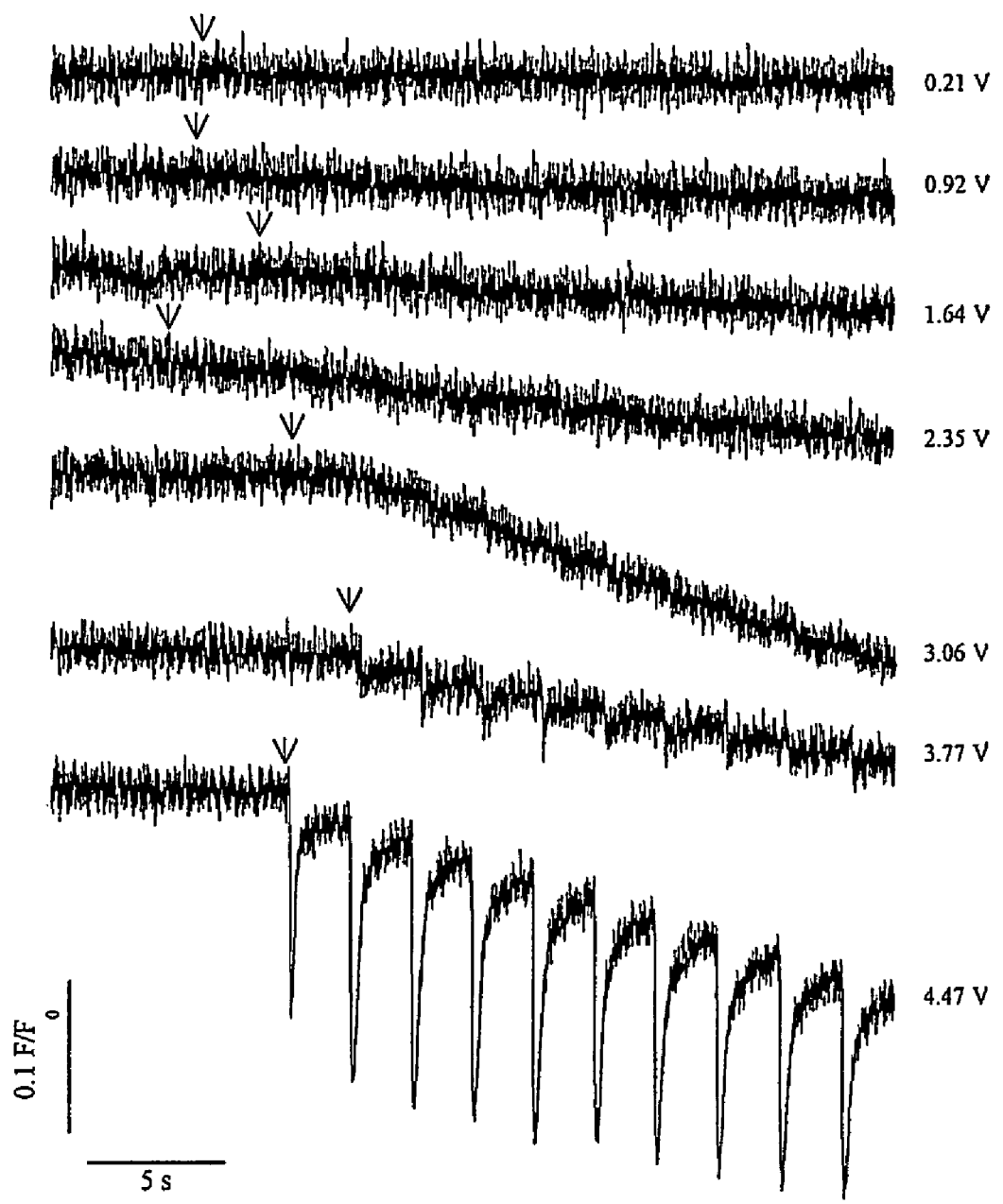
FIG. 6 shows the fluorescein emission (expressed as $F/F_0$) evaluated at a distance of 10 μm from the anode against time for peak field strengths rising from 0.21 to 4.47 V/100 μm for the myocyte of FIG. 5, demonstrating a change in local pH at elevated voltages.

To verify the acidification of the isolated microdroplet we monitored the extracellular pH with fluorescein. FIG. 6 shows the fluorescein emission (expressed as $F/F_0$, where F is the fluorescence recorded during the course of the experiment and $F_0$ is the fluorescence at t=0) evaluated at a distance of 10 µm from the anode against time for peak field strengths rising from 0.21 to 4.47 V/100 µm. The arrows indicate when voltage pulsing began (pulse width 6 ms, frequency 0.6 Hz).

The major species of this proteolytic acid between pH 5.5 and 7.0 are the di- and the monoanion, but only the dianion emits light with high quantum yield (0.9) upon excitation with 490 nm light. The pKa of 6.7 for the transition from the mono- to the dianion allows the decay of the emission to be correlated with the lowering of the pH in the range from pH 7 to pH 6.

As the peak electrical field rose in strength from 0.21 V/100 µm (i.e. 21 V/cm) to 4.47 V/100 µm (447 V/cm) a permanent lowering of the measured pH occurred (i.e. the solution became more acidic). Spiking was superimposed at higher voltages.

Figure 7:
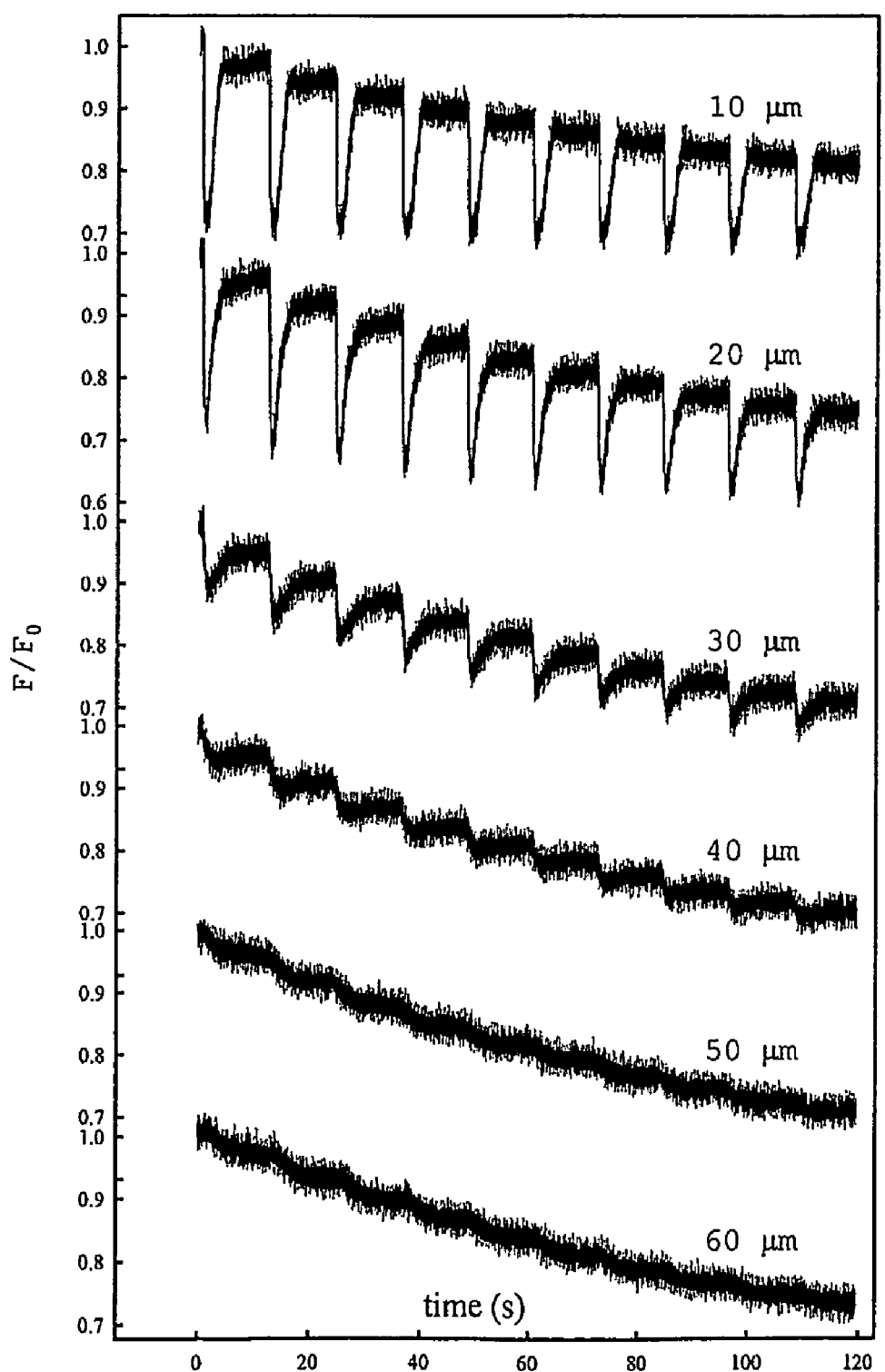
FIG. 7 shows the fluorescein emission evaluated at distances of from 10 to 60 μm from the anode against time for a peak field strength of 5.3 V/cm for the experimental arrangement of FIG. 6, demonstrating a change in local pH at elevated voltages

FIG. 7 shows the fluorescein emission evaluated at distances of from 10 to 60 µm from the anode against time for a peak field strength of 5.3 V/100 µm for the same experimental arrangement as FIG. 6. The spikes reduced in height with distance from the anode (and source of $H^+$).

Thus the extracellular pH only stayed unchanged in the test solution at peak field strengths of below 1 V/100 µm (which was, however, strong enough for pacing to occur). This illustrates the importance of operating the stimulating electrodes in a voltage range which is high enough for continued pacing and low enough to avoid electrolysis. However, the high voltage end of the range can be extended by providing a suitable coating on the electrodes, as discussed above.

Figure 8:
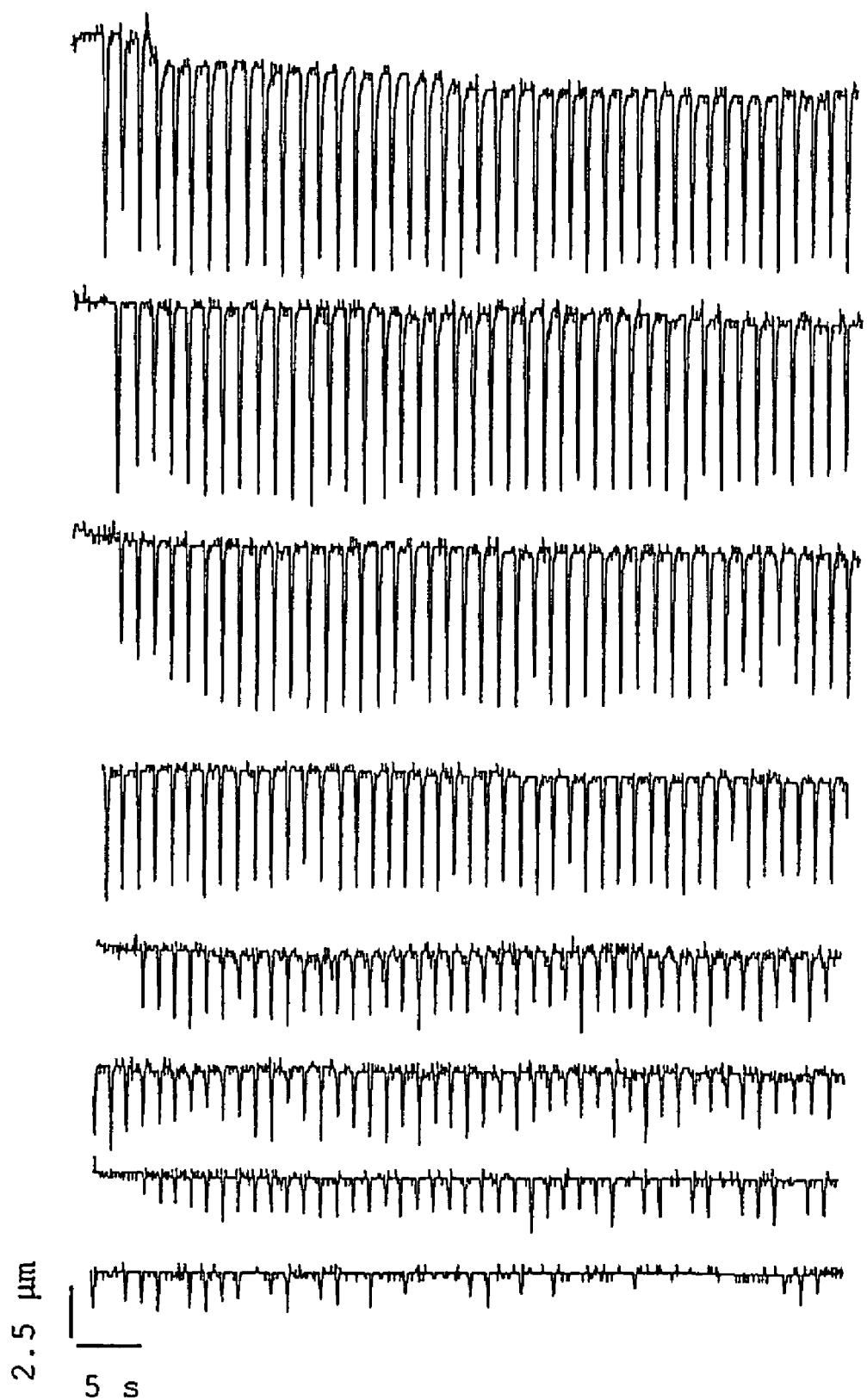
FIG. 8 shows a time course for a cell in an isolated microdroplet stimulated with a pulsed 0.9 V/100 μm amplitude electrical field until the beat ceased after about 6 min.

FIG. 8 shows a time course for a cell in an isolated microdroplet stimulated with a pulsed 0.9 V/100 µm amplitude electrical field until the beat ceased after about 6 min. The contractions displayed lowering amplitude over time, but no sudden stop as was seen with the extracellular pH drop of FIG. 5. We believe that the slow decay of contraction amplitude was caused by the irreversible consumption of ATP. This, therefore, demonstrates the importance of replenishing the supply of nutrients and removing waste products, through the flow channel.

To obtain information about $[Ca^{2+}]_i$ cycling between different cell compartments we monitored the emission of a paced fura-2 loaded cell at room temperature. Precautions were taken to ensure that pH and nutrition changes in the cell microdroplet were sufficiently small not to affect the cell during the course of pacing. The pacing was provided by 0.9 V/100 µm peak amplitude, 6 ms duration pulses at a frequency of 0.6 Hz, and continued for a 3 s excitation period.

Figure 9:
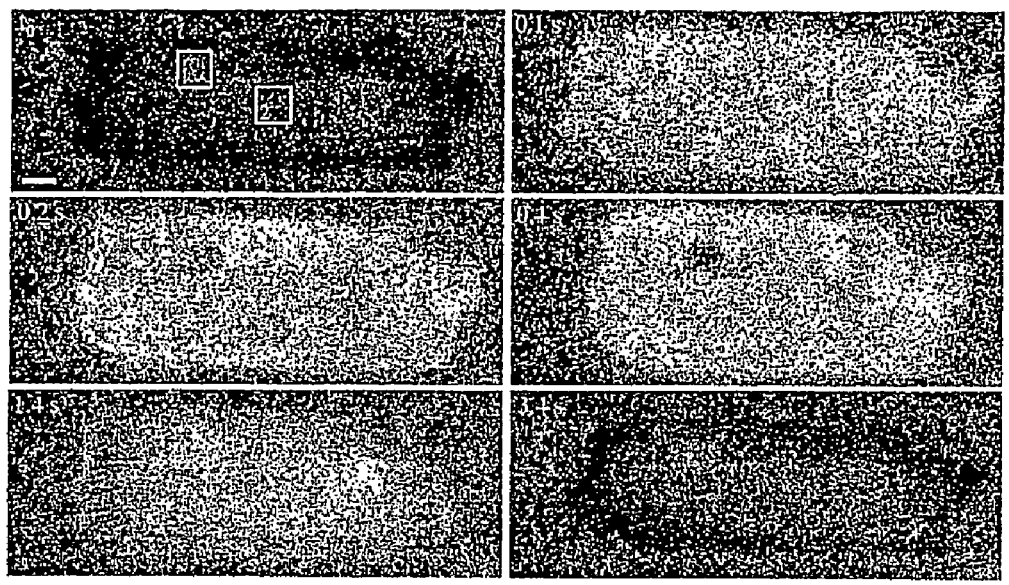
FIG. 9 shows the colour-coded changes in $[Ca^{2+}]_i$ before, during and after a 3 s excitation period in which cell pacing was provided by 0.9 V peak amplitude pulses across 100 μm electrode separation, the pulses being of 6 ms duration at a frequency of 0.6 Hz.

FIG. 9 shows the colour-coded changes in $[Ca^{2+}]_i$ before, during and after the excitation period. At rest ($t_0$) the fluorochrome is nearly homogenous distributed within the cytoplasm but its concentration is enriched in the two nuclei and reduced at both cell ends. Some higher affinity to longitudinal structures is observed. 0.1 s after the onset of the excitation period the $[Ca^{2+}]_i$ rose inhomogeneously with high $[Ca^{2+}]_i$ at both cell ends and few alternating 10 µm wide bands of high and low $[Ca^{2+}]_i$ perpendicular to the long axis of the cell.

Confocal line scan images taken during the excitation of a ventricular myocyte show a similar pattern of $[Ca^{2+}]_i$ changes. In heart muscle cells the tight coupling between the action potential and contraction (Excitation-Contraction coupling, E-C coupling) is mediated by a specialized intracellular $Ca^{2+}$ storage compartment, the sarcoplasmic reticulum (SR). Stored $Ca^{2+}$ leaves the organell through $Ca^{2+}$ release channels (Ryanodine sensitve $Ca^{2+}$ channel) which are activated through extracellular $Ca^{2+}$ entering the cytosol through voltage sensitive $Ca^{2+}$ channels which are themselves activated during the depolarisation of the sarcoleemm. The released $Ca^{2+}$ activates the contractile filaments to start the shortening of the myocyte (systole). Reuptake by the means of $Ca^{2+}$ pumping molecules (SERCA pump) residing in the SR membrane clears the cytosol from $Ca^{2+}$ so that the filaments can relax (diastole) until the next action potential starts another $Ca^{2+}$ cycle.

The inhomogenous rise of $[Ca^{2+}]_i$ shown in FIG. 9 within the first ms after the electrical stimulation is possibly indicating initiations sites ($Ca^{2+}$ sparks) which avalanche-like sum up with time to a global uniform rise of $[Ca^{2+}]_i$ to ensure the synchronized contraction of the entire cell. Failure of the coordinated $Ca^{2+}$ release is the molecular basis for several forms of arrhythms and the molecules involved in the E-C coupling are targets for drug candidates to treat heart diseases caused by this kind of arrhythmia.

0.2 s after the onset of the excitation period these bands disappeared and one of the nuclei displayed a higher $[Ca^{2+}]_i$ compared to the bulk of the cytosol.

The emission changes of the fluorochrome enriched in longitudinal structures followed those between these structures. Any brightness difference here is not due to differences in the $[Ca^{2+}]_i$ but is an artefact caused by the higher affinity of the fluorochrome to intracellular constituents. At 3.4 s (i.e. 0.4 s after the end of the excitation period) the $[Ca^{2+}]_i$ reached the $t_0$ (resting) level.

Figure 10:
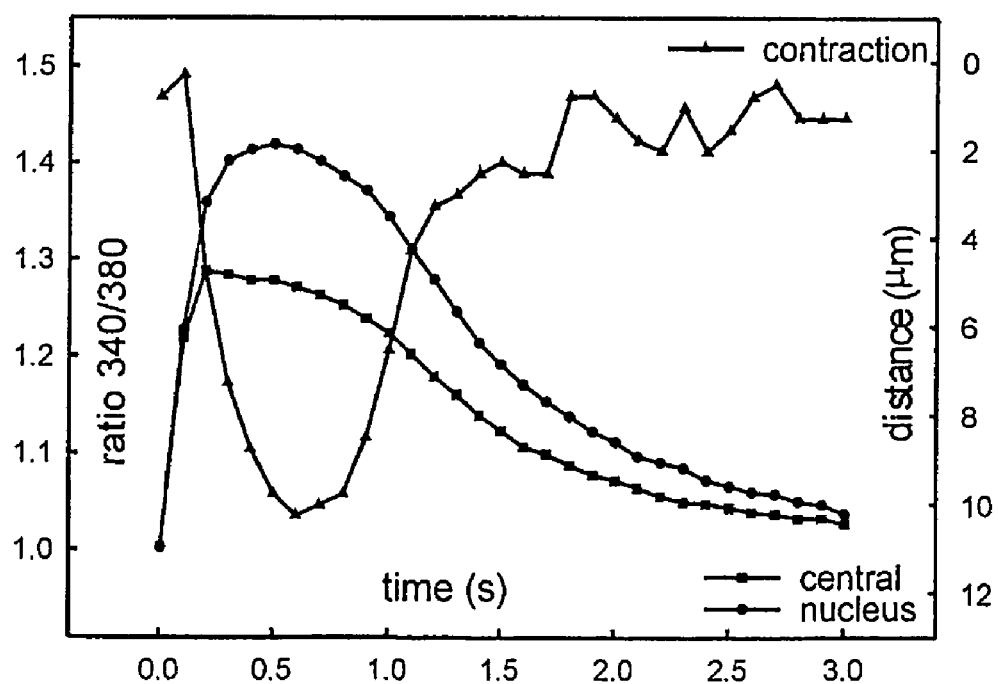
FIG. 10 shows the respective time courses of $[Ca^{2+}]_i$ at the cell left nucleus and centre (indicated by squares 1 and 2 in FIG. 9), together with the contraction time course of the left end of the cell, for the experimental arrangement of FIG. 9, FIGS. 11a and b show schematically the microfabrication process for a further device.

FIG. 10 shows the respective time courses of $[Ca^{2+}]_i$ at the cell left nucleus and centre (indicated by squares 1 and 2 in FIG. 9), together with the contraction time course of the left end of the cell. The onset of the contraction was about 100 ms later than the first visible rise of the $[Ca^{2+}]_i$, a delay which might be reduced at higher temperatures.

These results show that useful measurements can be obtained from cells using a cell assay device according to the present invention.

In particular, the high spatial and temporal resolution of the implemented imaging system in conjunction with a state of the art optical microscope enables the device to perform optical-assays of the $[Ca^{2+}]_i$ changes in individual living cells during electrical stimulation. Because of the tight coupling between the action potential and the rise of $[Ca^{2+}]_i$ in excitable cells the time course and amplitude of the evoked $Ca^{2+}$ transient is a reliable indicator of the corresponding parameter of the underlying action potential. Thus the device can reveal the response of the ion channel activity within the cell membrane to different stimulus protocols. Preferably, the pulse generator comprises a program to run a protocol with either automatically rising or lowering the pulse amplitude, pulse frequency, pulse width, or with automatically varying the pulse polarity either between individual pulses or between unipolar and bipolar (symmetric or asymmetric) pulses.

The device also enables the direct detection of the membrane potential changes with potential sensitive dyes like Di-8-ANEPPS or RH-237 (Molecular Probes) in response to the aforementioned stimulus protocol.

By means of the flow channel the metabolic state of the stimulated cell can be changed so that the cellular response to an intermittent period of for example glucose deprivation can be studied.

EXAMPLE 2

Device Fabrication

Figure 11:
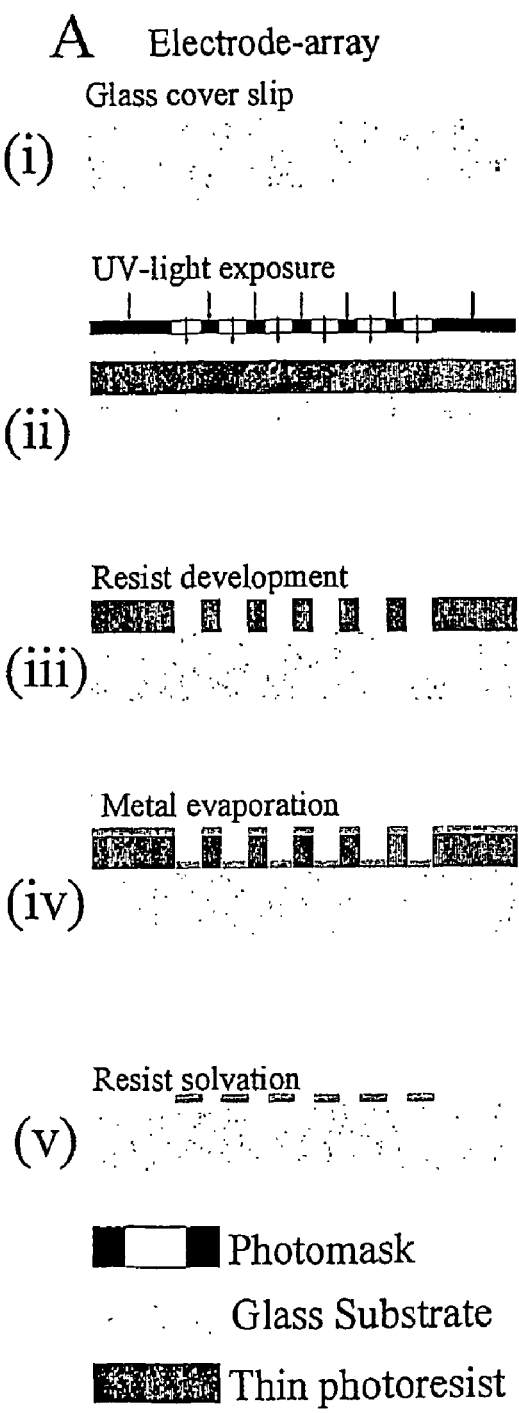
Figure 11:
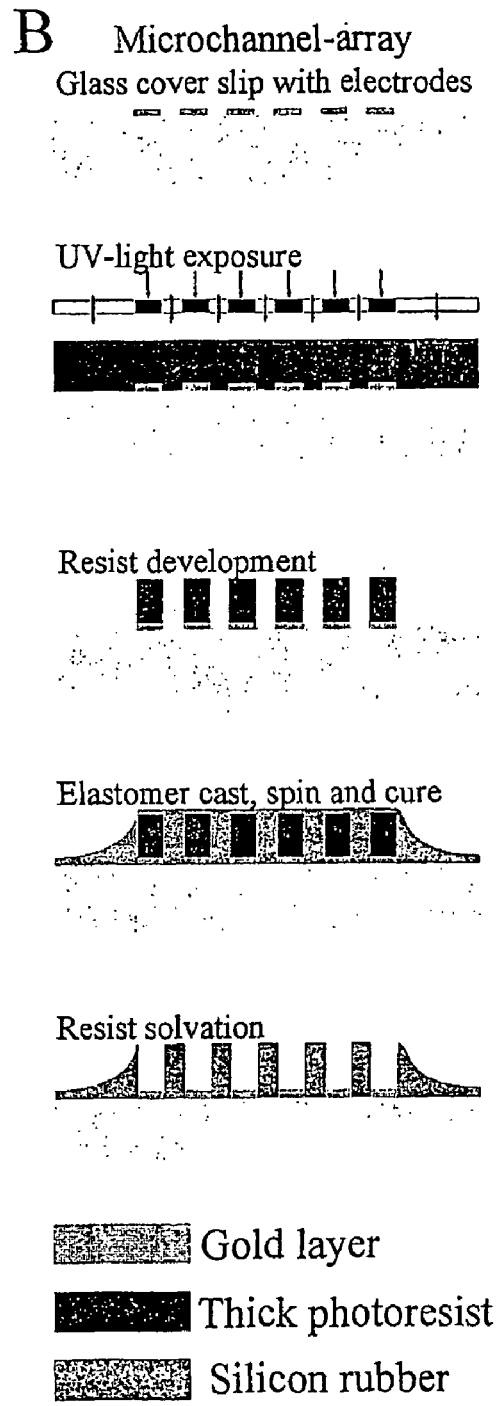

Microscope glass coverslips (24×40 mm, thickness No. 1, 0.13-0.17 mm) were used as substrates to allow the recording of the intra- and extracellular fluorescence as well as cellular morphology with oil and water immersion lenses (thereby enabling the use of lenses with a high numerical aperture and a low working distance of ~300 μm). The device microfabrication process is shown schematically in FIGS. 11a and b.

The patterns for microelectrodes and for the walls of micron-sized elongate chambers (i.e. confinement cavities) were both designed using AutoCAD and were produced as two chrome coated maskplates, using a Philips electron beam writer. To photolithographically pattern the microelectrode array, the coverslips (FIG. 11a(i)) were first spin-coated with the thin positive photoresist S1818 at 4000 rpm, baked in the oven at 90° C. for 30 min with an intermediate 15 min soak in chlorobenzene, and were then exposed to UV-light, through the appropriate photomask (FIG. 11a(ii)). The microelectrode array was then formed by the sequential electron beam assisted deposition of an adhesive layer of 10 nm titanium and an electrochemically stable overlayer of 100 nm gold (FIG. 11a(iv)). The microelectrode structures were realised by lifting-off unexposed metal coated photopolymer (FIG. 11a(v)). Visual inspection of the quality of the metal pattern was carried out using a 20× lens on an upright light microscope.

The microelectrode arrays were subsequently modified with a lithographically formed PDMS suprastructure, which defined the walls of microchambers, and which was produced as shown schematically in FIG. 11b. Firstly, a thick positive resist (AZ 4562) was spun at 1300 rpm to produce a ~10 μm thick photoresist layer, which was baked in the oven at 90° C. for 30 min. The thickness of the photoresist defined the depth of chambers. The appropriate photomask was aligned to the microelectrodes on a mask aligner and the pattern was transferred into the photoresist (FIG. 11b(ii)). After development, the arrays were spin coated at 10,000 rpm with a 1:4 dilution of PDMS in toluene and baked in the oven at 120° C. for about 2 min to cure the PDMS (FIG. 11b(iv)). The PDMS was thereby molded against a photoresist master and the whole assembly was thoroughly washed in acetone. This latter step removed all residual resist from the chamber walls and from the surface of the microelectrodes. Without the support of the photoresist, the thin film of PDMS covering the chambers collapsed and was easily washed off. The PDMS film covering the bulk electrodes served as an insulating layer to avoid short circuits of the connecting leads through buffer spill.

To fill the microchambers with aqueous buffer solution, the hydrophobic surface of the PDMS was wetted with ethanol, which was gradually replaced by water. After filling the chambers with an appropriate buffer solution, they were then covered with a 300 μm layer of mineral oil to avoid evaporation.

The patterned substrates were then connected to a PCB in the manner described above in relation to FIG. 1b of Experiment 1.

Figure 12:
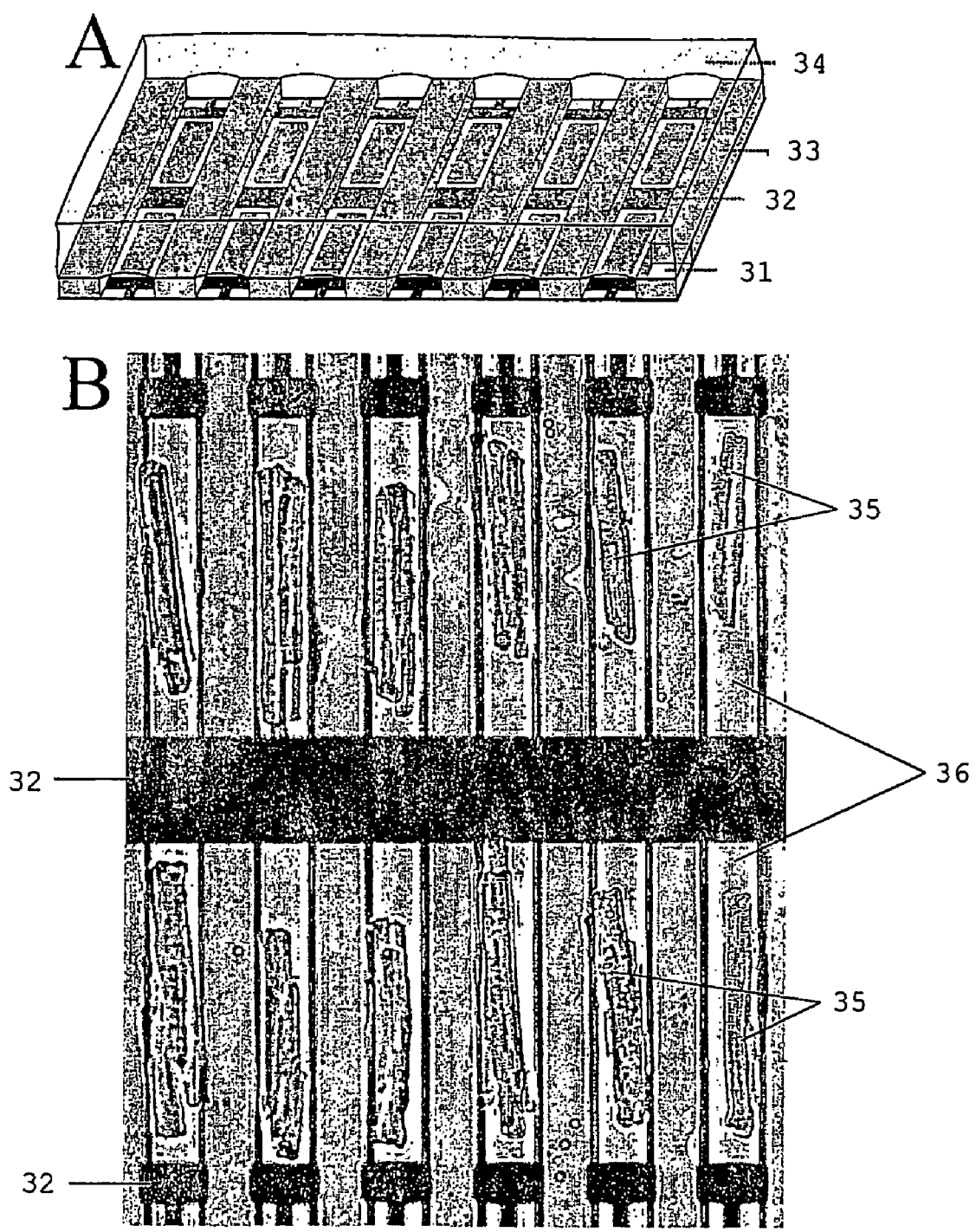
FIG. 12a is a schematic diagram of the patterned microarray formed by the process of FIGS. 11a and b.
FIG. 12b shows a micrograph of the microarray with myocytes positioned in the chambers of the array.

FIG. 12a is a schematic diagram of a microarray formed by the patterning process and shows the glass coverslip 31, gold electrode 32, PDMS chamber side wall 33, and mineral oil 34.

Isolation of Cardiomyocytes

This was performed as described above in relation to Experiment 1.

Myocyte Selection and Placement

Individual adult ventricular myocytes in the cell suspension were field stimulated with platinum macroelectrodes at 0.5 Hz, and were transferred to the microarray on the basis of several criteria, namely: that they responded faithfully to a low amplitude stimulus (5 V/cm) with regular and uniform shortening; that they had regular and clearly defined striation patterns with no obvious signs of damage in the intercalated disc regions; and were 20-30 μm wide and 140-180 μm long. Cells were initially pipetted into a microdroplet on top of the micro-array by means of a capillary connected to a syringe pump and roughly aligned with their long axes parallel to the elongate microchambers. Removing the excess of fluid from the hydrophobic PDMS-surface guided the myocytes into the chambers between the electrodes. FIG. 12b shows a micrograph of the microarray with the myocytes 35 positioned in the chambers 36 and aligned to the microelectrodes 32.

Microarray Geometry

The reported field strengths required to electrically stimulate ventricular cardiomyocytes are in the range of 5-50 V/cm (P. A. Gomes, R. A. Bassani and J. W. M. Bassani, 2001, *Electric field stimulation of cardiac myocytes during postnatal development*, IEEE Transactions on Biomedical Engineering, 48, 630-636). However the use of voltages above about 1 V leads to local electrolysis in proximity to the electrode, resulting in the generation of ionic species that can change the pH of the bathing solution. In the present experiment, the electrodes were arranged such that an average sized ventricular myocyte (approximately 160 μm in length, 25 μm in width and 5 μm in height) could be placed between two electrodes. For example, fields of the order of 25 V/cm could be readily achieved across each myocyte by applying a voltage of 0.5 V across two microelectrodes, placed 200 μm apart.

Previous reports suggest that an electric field will be more effective in inducing contraction when oriented parallel rather than orthogonal to the length of the myocyte (L. Tung, N. Sliz and M. R. Mulligan, 1991, *Influence of electrical axis of stimulation on excitation of cardiac muscle cells*, Circ. Res., 69, 722-730.; and S. B. Knisley and A. O. Grant, 1995, *Asymmetrical electrically induced injury of rabbit ventricular myocytes*, J. Mol. Cell. Cardiol., 27, 1111-1122). Thus, to generate a field oriented parallel to the elongate chambers, the electrodes were formed to traverse the gap between the longitudinal chamber walls (see FIGS. 12a and b). A 60 μm wide central gold electrode crossing the middle of the array was used as the common reference electrode.

Stimulating electrodes were fabricated on both sides of and spaced from the reference electrode, allowing the placement of two single myocytes either side of the central electrode. This arrangement could be repeated to stimulate larger arrays of myocytes. Whilst the reference electrode was common to all the chambers, the peripheral stimulating electrodes were each individually addressable, in order to permit the sequential stimulation of individual cells with different field strengths and/or frequencies of stimulation.

The gap between each stimulating electrode and the reference electrode was 200 μm, which was large enough to provide an arena for single cell analysis whilst minimising the applied potential for field stimulation. The stimulating electrodes had dimensions of 40 μm width, 20 μm length and 100 nm height. The active surface area of each stimulation electrode was thus 800 μm².

Conditions for field stimulation were further optimized by minimizing the conducting volume between the electrodes. To this end, the height of the chamber was limited to 10 μm and width to 40 μm, dimensions only slightly larger than those of an isolated adult cardiac myocyte. The limited extracellular space restricted ionic current flow in the solution between the electrodes. The volume occupied by an average sized myocyte was about 20 pL.

Microarrays were produced with two chamber volumes. 100 pL chambers were generated by forming PDMS end walls adjacent each stimulating electrode and above the central reference electrode. Although not shown in FIGS. 11 and 12, the end walls were formed at the same time as the side walls. The end walls sealed each chamber to prevented fluid escape.

5 nL chambers were generated by omitting the end walls. As the side walls extended 2 mm beyond the stimulating electrodes, this gave a significantly larger chamber volume.

Intermediate chamber volumes could be generated simply by placing the end walls at different spacings from the stimulating electrodes.

Light Microscopy

Sarcomere length and intracellular $Ca^{2+}$ concentration ($[Ca^{2+}]_i$) were monitored simultaneous using the fluorescence-contractility System of Ionoptix (Milton, Mass., USA). Ventricular myocytes were loaded with Fluo-3 by incubation for 30 min in 20 µM Fluo-3 AM solution (Molecular Probes). The internal dye was excited at 505 nm with a TILL monochromator (T.I.L.L. Photonics, Martinsried, Germany) mounted on a Zeiss Axiovert 200 (Zeiss, Gottingen, Germany) equipped with a x63 C-Apochromat water immersion lens, NA 1.2. The emission of Fluo-3 was directed to the PMT-tube through a 510 dichroic mirror and a 515 bandpass filter (Omega Optical, Brattleboro, Vt., USA). The red light of the halogen lamp filtered through a 680 nm bandpass filter was directed to a CCD camera to record the sarcomere length. PMT and camera signals were displayed online with the IonWizard Version 5.0 software and stored for further evaluation. To measure the possible change in extracellular pH during field stimulation, 10 µM BCECF (Molecular Probes) was added to the bath and the emission was recorded using the same filter set as for Fluo-3. To avoid bleaching, BCECF was excited at 505 nm every 200 ms for 5 ms. The intensity of the excitation light for both dyes was adjusted by a neutral density filter (OD=2).

Confocal Microscopy

Confocal line scan images of intracellular Fluo-3 were recorded on a BioRad Radiance 2000 confocal scanner mounted to a Nikon inverted microscope (Eclipse) using a 60x Fluor water immersion objective (NA 1.2). The scan line was oriented parallel to the longitudinal axis of the myocytes and the emission recorded at 500 Hz. To mark the pulse arrival on the line scan image, a LED-flash of 2 ms duration aligned to the optical path of the microscope was triggered 25 ms before the stimulus pulse.

Separate confocal imaging measurements were made to examine the volume of ventricular myocytes in microchambers. Z-stacks (0.5 µm spacing) were recorded on the same microscope. $Ca^{2+}$ saturated Fluo-3 was added to the bath and the extracellular dye was excited at 810 nm using a 700 mW Mira laser system (Coherent Lasers USA). Z-stacks were used to construct 3D views of the myocytes and to calculate the extracellular volume in the microchamber using the Huygens software (Bitplane, Switzerland).

Electrical Stimulation

Symmetric biphasic rectangular pulses were generated across the electrodes. Each phase was individually controlled according to amplitude, duration, polarity, frequency and delay between the two phases. A voltage-current converter was used to read the current response of one electrode together with the corresponding voltage into a 20 MHz 4 channel acquisition card (PCI-9812, Adlink, Taiwan). A TTL signal synchronous to the biphasic pulses was fed into the reader of the PMT-current to mark each pulse arrival on the fluorescence trace for off-line event averaging. After filling the microchambers with electrolyte (buffer), the current evoked on the individual stimulation electrodes was monitored to assure the ionic connection between the microelectrodes in each chamber, prior to the addition of cardiac muscle cells. The measured current was integrated to give a measure of the total amount of net-charge added to the microchamber, and the polarization of the electrode surface.

Figure 13:
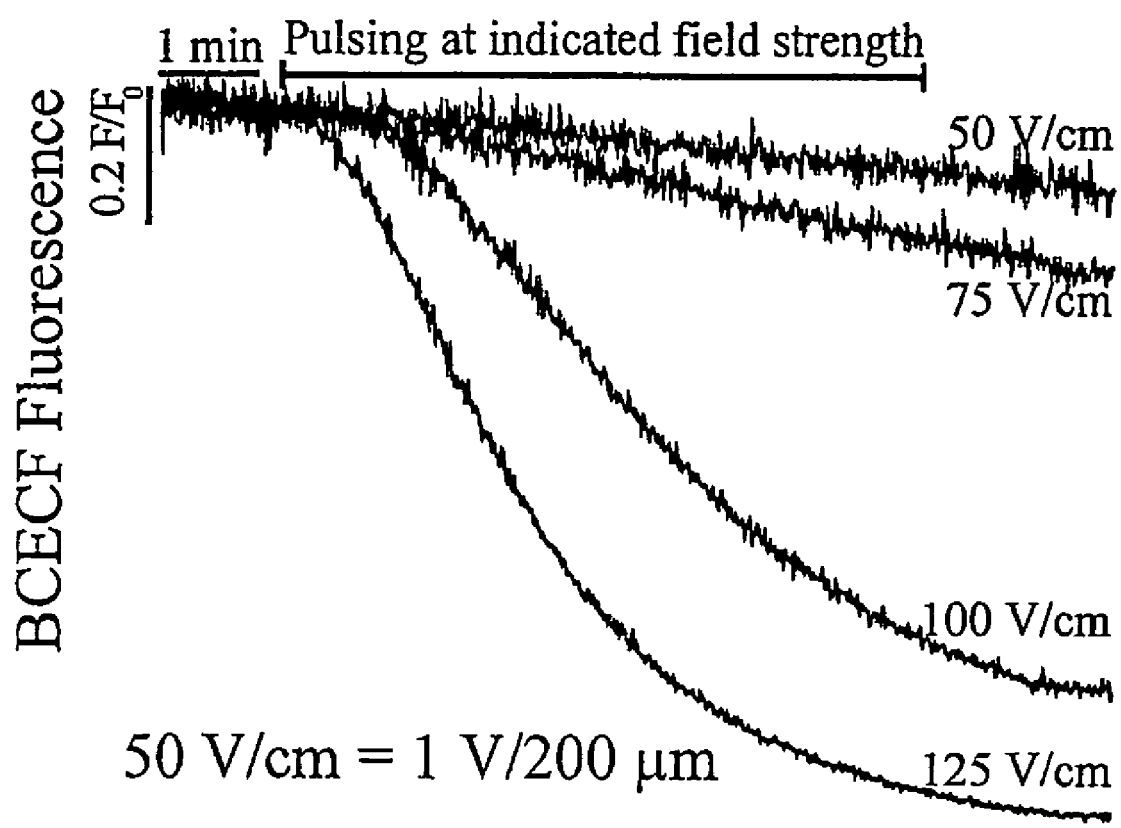
FIG. 13 shows a plot of BCECF fluorescence against time at the indicated filed strengths for electrolyte contained in a chamber of the microarray of FIGS. 12a and b.

Given the extremely small chamber volumes, any electrolysis products (e.g. $Au^+$, $H^+$) generated on the electrode surface will accumulate rapidly over time. To check for accumulation of $H^+$ ions, the chambers were filled with 100 pL of the electrolyte buffered with 1 mM HEPES containing the pH sensitive dye BCECF (20 µM). Unipolar rectangle pulses of 2 ms duration and amplitudes between 0.5 V (50V/cm) and 2.5 V (125 V/cm) were applied at 1.5 Hz to the integrated electrodes. As shown in FIG. 13 the pH did not change using stimulus voltages close to the theoretical threshold for hydrolysis (0.8 V, 40 V/cm), although the pH was seen to drop rapidly at voltages above the theoretically predicted thresholds. When pulsed with amplitudes of >2.0 V (>100 V/cm) across the 200 µm distance between the electrodes, the pH reached a steady-state within 10 min of continual pulsing at 1.5 Hz and did not recover after the pulses were stopped. No bubble formation or signs of pH dependent dissolution of the gold were observed during the experiment. The average field strength required to illicit stable $Ca^{2+}$ transients in single cardiac myocytes of average length ~160 µm was 27 V/cm ±10 V/cm. This was well below the field strengths necessary for electrolysis (>40 V/cm). It was also less than the >50 V/cm field strengths necessary to electroporate cardiac myocyte membranes (with resultant irreversible breakdown of the sarcolemma, inward $Ca^{2+}$ leakage and the development of a hypercontracture)

Sychronous Activation of Myocytes

The pulsing regime was optimized by comparing the threshold stimulation current at different stimulus profiles. The "all or none" response of the action potential helped to identify the limit for a supra-threshold stimulus, by gradually increasing the amplitude of the pulse. The action potential was measured either directly with the voltage-sensitive dye Di-8-ANNEPPS or indirectly, by recording $Ca^{2+}$ transients or cell shortening. The optimized pulse profile comprised a symmetric biphasic rectangular stimulus with 2 ms duration and 0.5 V amplitude per phase. The steady-state current passed between the electrodes was less than 2 nA and polarization of the electrodes was negligible.

Figure 14:
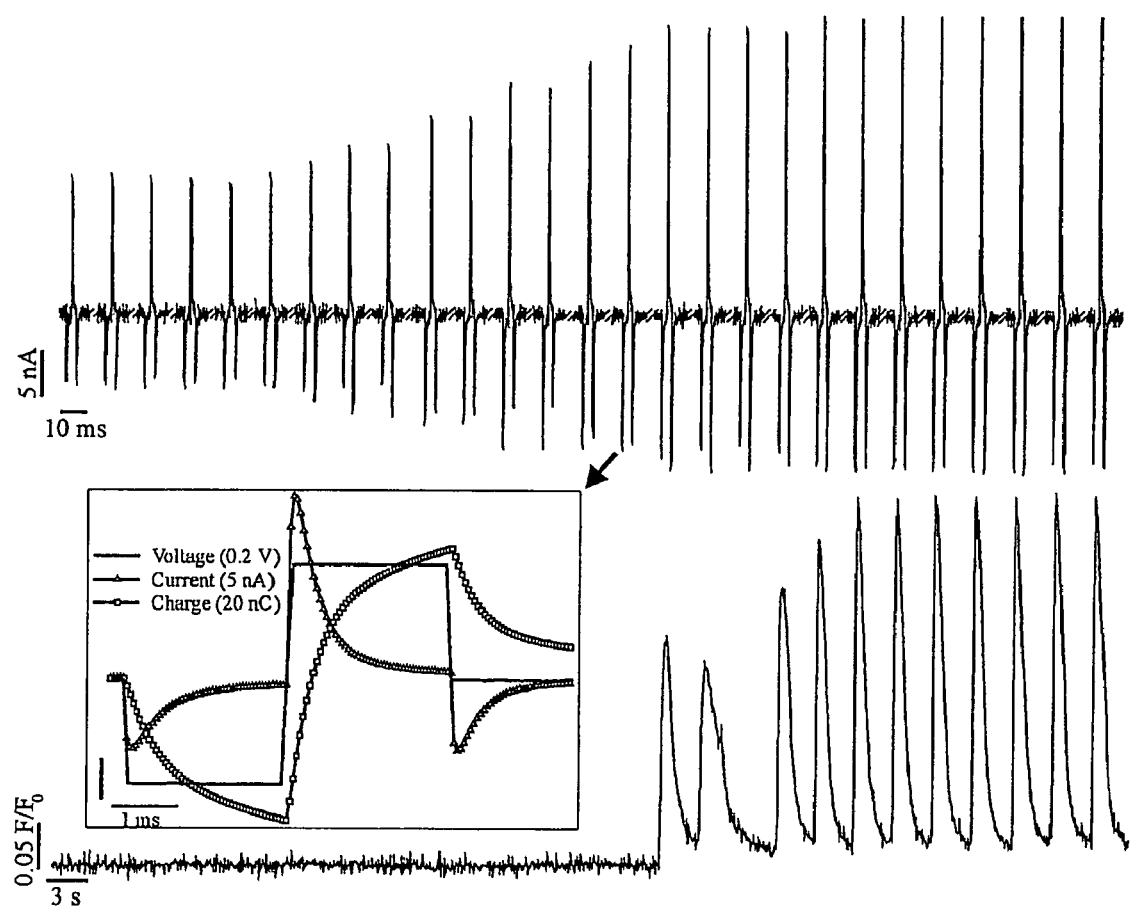
FIG. 14 shows typical stimulation (upper) and response (lower) traces for a myocyte contained in a chamber of the microarray of FIGS. 12a and b.

FIG. 14 shows typical stimulation and response traces. The top trace shows the train of current spikes recorded on one of the stimulating electrodes. The bottom trace shows the concurrent intracellular $Ca^{2+}$ transients occurring only after suprathreshold stimulation. The amplitude of the stimulus was gradually increased until the first $Ca^{2+}$ transient was triggered. The inset shows the last current spike before the onset of excitation on an expanded time-scale together with the correspondent voltage and charge profile. The $Ca^{2+}$ transients were recorded with the $Ca^{2+}$-sensitive dye Fluo-3.

Figure 15:
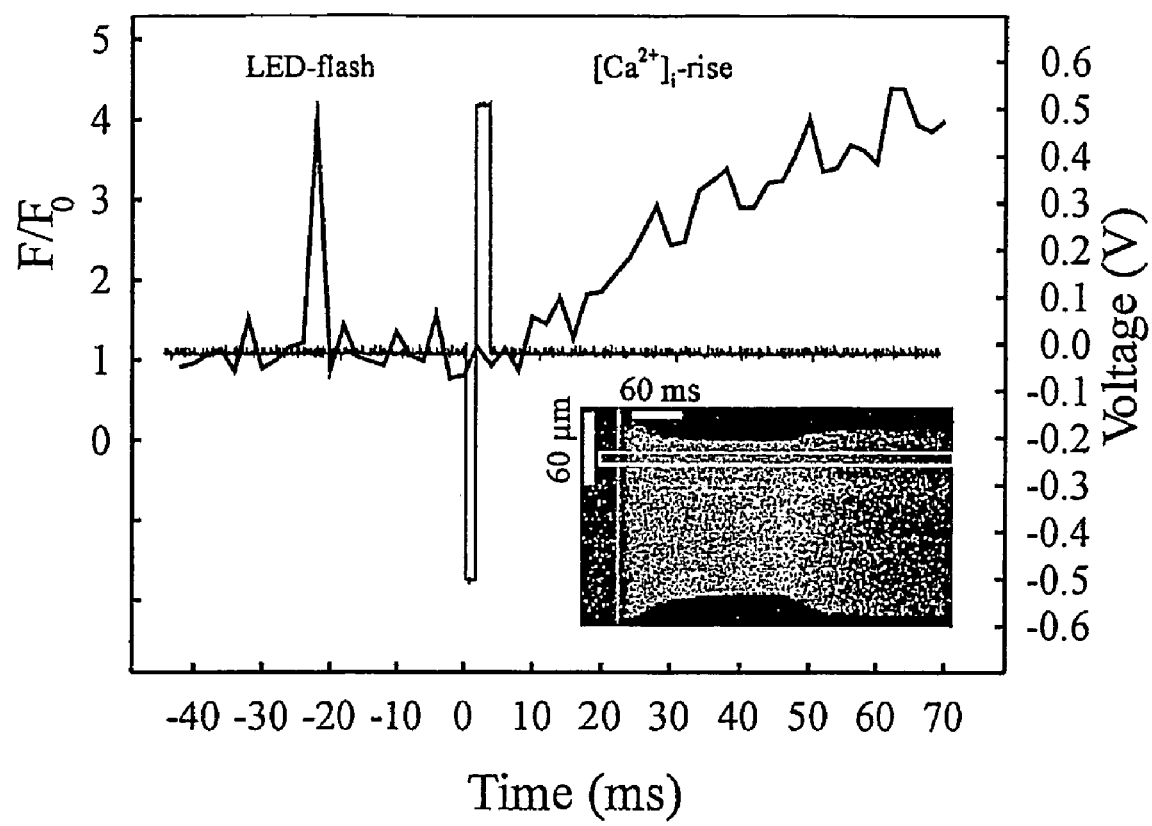
FIG. 15 shows high resolution voltage (thin line) and fluorescence (thick line) traces for a single pulse event, FIGS. 16a and b respectively show superimposed records of relative sarcomere length from myocytes stimulated in 5 nL chamber and 100 pL chambers.

To further characterize the intracellular $Ca^{2+}$ fluxes implicated in excitation-contraction coupling, the electrically stimulated $Ca^{2+}$ transients were recorded confocally with high spatial and temporal resolution. The Fluo-3 loaded cells were placed into the microchambers. A pre-pulse to trigger a 2 ms LED flash was added 25 ms in advance to the stimulating pulse to mark the arrival of the latter on the confocal line scan image. Cells were stimulated at 0.5 Hz and a representative transient is provided in FIG. 15 which shows the uniform rise of $[Ca^{2+}]_i$ upon electrical stimulation with microelectrodes. In relation to FIG. 15 the confocal scan line was aligned to the longitudinal axis of the Fluo-3 loaded cell (shown in the insert) paced with biphasic stimuli. The acquired line scan image shows the uniform rise in $[Ca^{2+}]_i$ immediately after the excitation. Note the cell shortening in response to the $[Ca^{2+}]_i$ rise and relaxation after the $Ca^{2+}$-clearance. The fluorescence profile in a 10 μm wide band (indicated) is plotted against time (thick line) together with the voltage profile of the stimulator (thin line).

The instantaneous uniform rise of $[Ca^{2+}]_i$ as revealed on the scan along the longitudinal axis of the cell evoked the shortening of both ends of the adult ventricular myocyte. The time resolution of 2 ms/scan did not enable the identification of the triggering phase of the stimulus (make or break stimulation). Given an intra/extracellular resistivity of 500 $\Omega cm^{-1}$ (S. Weidmann, 1970, *Electrical constants of trabecular muscle from mammalian heart*, J. Physiol., 210, 1041-1054) and a membrane capacitance of 1 $\mu Fcm^{-2}$, it is likely that charging of the cell membrane occurred in a few microseconds.

Prolonged Stimulation

Figure 16:
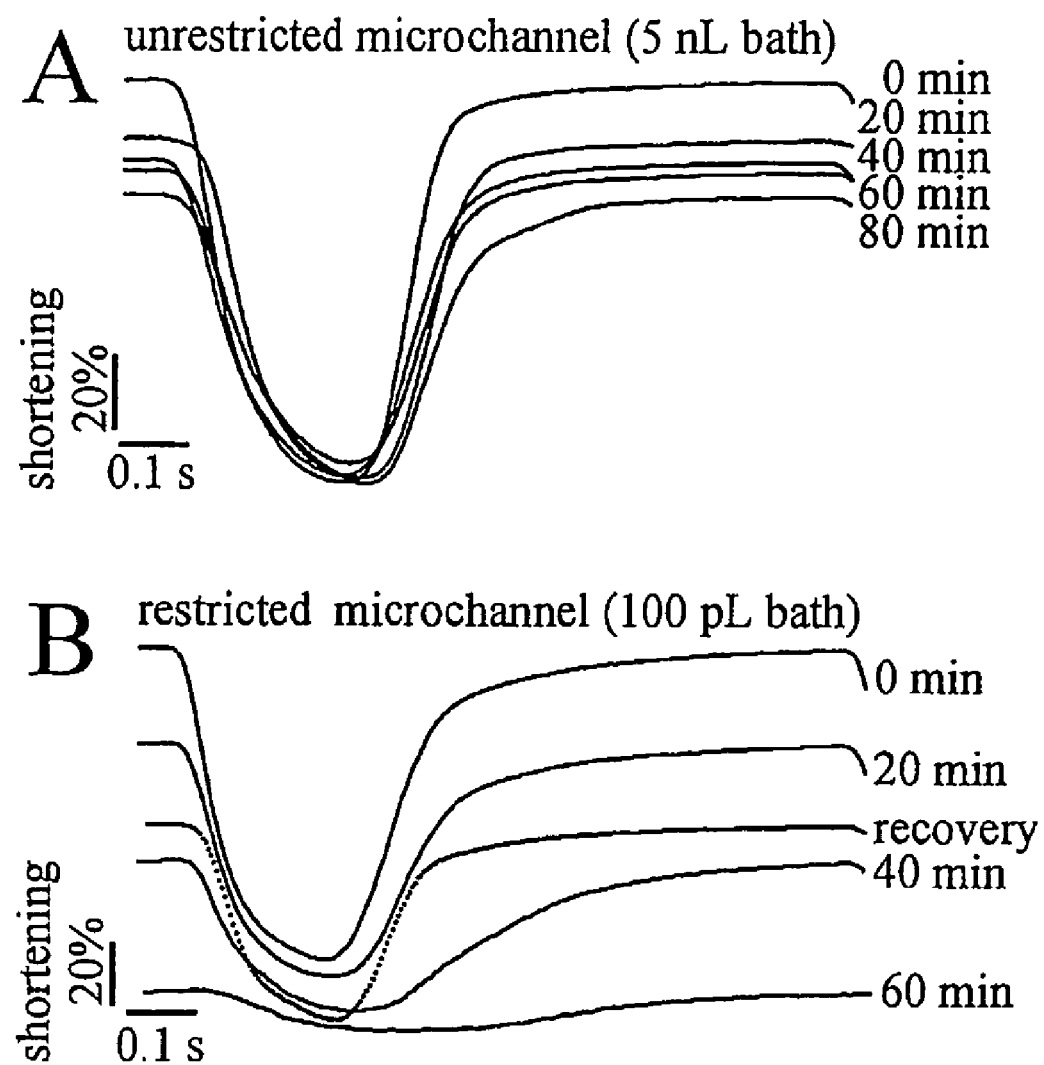

Adult ventricular myocytes were continually stimulated in the microchambers of volumes 5 nL and 100 pL. Myocyte contractility was measured as the change of the sarcomere length from cardiomyocytes stimulated at 1 Hz (19-21° C.). FIG. 16a shows superimposed records of relative sarcomere length from a myocyte stimulated in the 5 nL chamber, single transients from a continuous record being shown. The time values on the right hand side are the period from development of steady-state shortening. FIG. 16b shows the corresponding records for a myocyte stimulated in the 100 pL chamber. In the 5 nL chamber, the amplitude of the cell shortening decreased to a small extent during continual stimulation (FIG. 16a). However, in the restricted volume 100 pL chamber, the cellular cell shortening ceased after 60 min continual pacing and partially recovered after renewal of the buffer (FIG. 16b). The average decline in cell shortening under these two conditions is shown in Table 1.

TABLE 1

|  | % of cell shortening | |
| --- | --- | --- |
| Min of pacing | 5 nL chamber | 100 pL chamber |
| 0 | 100 | 100 |
| 15 | 83 ± 12 | 79 ± 19 |
| 20 | 74 ± 6 | 73 ± 9 |
| 30 | 69 ± 11 | 39 ± 16 |
| 40 | 68 ± 13 | 30 ± 4 |
| 50 | 68 ± 25 | 13 |
| 60 | 61 + 27 | — |

Figure 17:
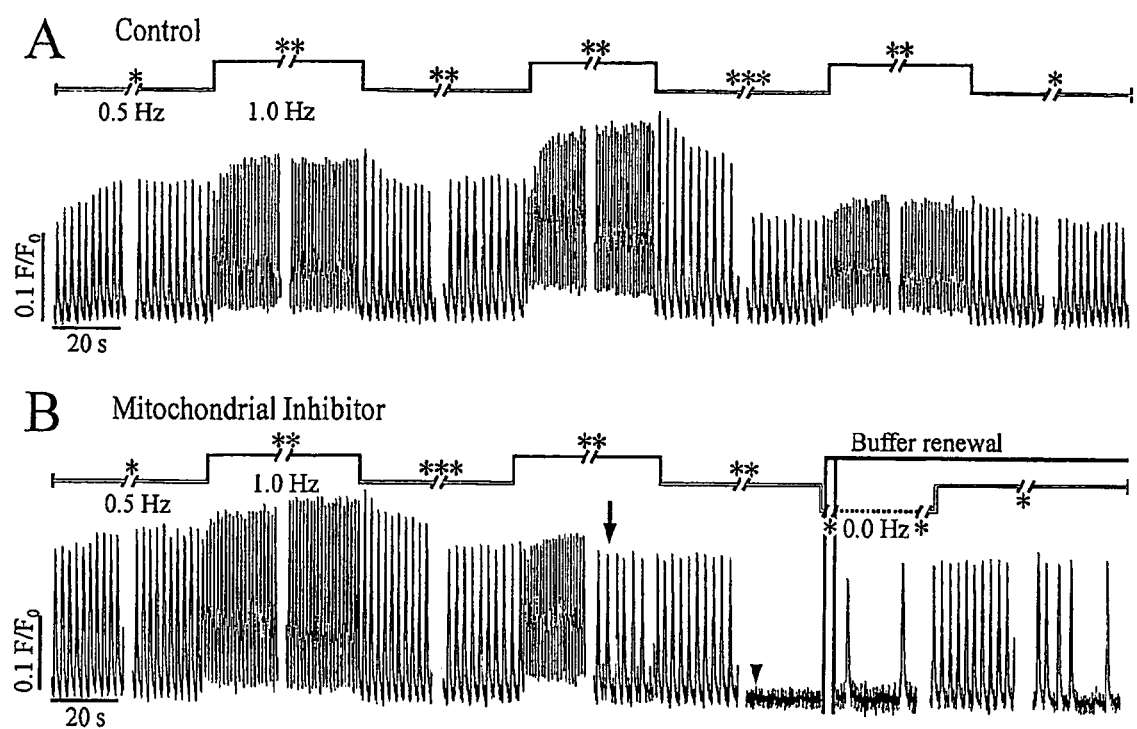
FIG. 17a shows the fluorescence caused by $Ca^{2+}$ transients from a myocyte electrically stimulated at alternating frequencies of 0.5 Hz (white bar) and 1.0 Hz (black bar) for periods of 5 (*), 10 () or 20 (*) min.
FIG. 17b shows the corresponding fluorescence for a myocyte stimulated in the presence of 1 μM FCCP.

In separate experiments, the $Ca^{2+}$ transients were measured from continually paced adult ventricular Fluo-3 loaded myocytes in the restricted volume 100 pL chambers. FIG. 17a shows the fluoroscence caused by the transients recorded at 50 Hz with an intensified CCD camera. The cells were electrically stimulated at alternating frequencies of 0.5 Hz (white bar) and 1.0 Hz (black bar) for periods of 5 (*), 10 () or 20 (*) min. The diastolic $[Ca^{2+}]$ signal adapted. almost instantaneously to higher levels at higher frequencies whereas the peak of the $Ca^{2+}$ transient reached steady-state after the first 5 beats at the higher frequency. Returning to lower frequencies returned the diastolic level to the lower value. The amplitude of the $Ca^{2+}$ signal decreased slowly over ~60 min of stimulation. This decrease was less than the attenuation of the shortening signal (FIG. 16a, Table 1). While this may represent a decrease of the intracellular $Ca^{2+}$, dye bleaching or dye loss/sequestration may also contribute.

A similar response was observed in cells paced in the presence of 1 μM FCCP, a mitochondrial uncoupler which induces intracellular ATP-depletion (FIG. 17b). After 50 min continual stimulation at alternating frequencies of 0.5 and 1.0 Hz (arrow) the cell no longer responded to every single stimulus with a $Ca^{2+}$ transient of normal amplitude. 10 minutes later (arrowhead) the $Ca^{2+}$ transients evoked at 0.5 Hz ceased almost completely.

$Ca^{2+}$ waves with low frequency were observed after washing out FCCP and changing the buffer (FIG. 17b). The cell regained its excitability after a 5 min rest interval between the continuous stimulation indicating the integrity of the sarcolemma.

In any event, loss of excitability during continual stimulation was likely caused by cellular by-products accumulating in the intra- and extracellular space rather than by extracellular acidification (cf. FIG. 13).

In summary, the experiments illustrate the feasibility of stimulating isolated cells within limited volumes in an array format.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All the publications mentioned above are hereby incorporated by reference.

The invention claimed is:

1. A device for performing cell assays, which device has at least one assay site, the site comprising a pair of stimulating electrodes, a cell confinement cavity for confining at least one cell in an extracellular fluid medium, and one or more sensor electrodes, the cell confinement cavity and the stimulating electrodes being arranged so that, in use, each cell is exposable to an electrical field generated by a potential difference applied across the stimulating electrodes, wherein the stimulating electrodes are spaced a distance apart such that the potential difference can induce field stimulation of each cell and simultaneously be below the level that would result in electrolysis of the extracellular fluid medium, and in which the electrical field includes a region of substantially uniform electrical field, each confined cell being exposable to the region, and in which the region of substantially uniform electrical field is bounded at one side by the floor of the cell confinement cavity.

2. A device according to claim 1, in which in the region of substantially uniform electrical field the electrical field strength varies transversely to the electrical field lines by no more than 10%.

3. A device according to claim 1, in which the region of substantially uniform electrical field extends along and/or transversely to the direction of the electrical field lines for a distance at least 2 μm.

4. A device according to claim 1, in which the region of substantially uniform electrical field occupies a volume of at least 1 pL.

5. A device for performing cell assays, which device has at least one assay site, the site comprising a pair of stimulating electrodes, a cell confinement cavity for confining at least one cell in an extracellular fluid medium, and one or more sensor electrodes, the cell confinement cavity and the stimulating electrodes being arranged so that, in use, each cell is exposable to an electrical field generated by a potential difference applied across the stimulating electrodes, wherein the stimulating electrodes are spaced a distance apart such that the potential difference can induce field stimulation of each cell and simultaneously be below the level that would result in electrolysis of the extracellular fluid medium, and in which the stimulating electrodes are coated with a chargeable surface area enhancing agent.

6. A device for performing cell assays, which device has at least one assay site, the site comprising a pair of stimulating electrodes, a cell confinement cavity for confining at least one cell, and one or more sensor electrodes, the cell confinement cavity and the stimulating electrodes being arranged so that, in use, each cell is exposable to an electrical field generated by the stimulating electrodes, wherein the device further comprises at least one flow channel which is in fluid communication with the confinement cavity, and in which the electrical field includes a region of substantially uniform electrical field, each confined cell being exposable to the region, and in which the region of substantially uniform electrical field is bounded at one side by the floor of the cell confinement cavity.

7. A device according to claim 6, in which in the region of substantially uniform electrical field the electrical field strength varies transversely to the electrical field lines by no more than 10%.

8. A device according to claim 6, in which the region of substantially uniform electrical field extends along and/or transversely to the direction of the electrical field lines for a distance at least 2 µm.

9. A device according to claim 6, in which the region of substantially uniform electrical field occupies a volume of at least 1 pL.

10. A device for performing cell assays, which device has at least one assay site, the site comprising a pair of stimulating electrodes, a cell confinement cavity for confining at least one cell, and one or more sensor electrodes, the cell confinement cavity and the stimulating electrodes being arranged so that, in use, each cell is exposable to an electrical field generated by the stimulating electrodes, wherein the device further comprises at least one flow channel which is in fluid communication with the confinement cavity, and in which the stimulating electrodes are coated with a chargeable surface area enhancing agent.

11. A device for performing cell assays, which device has at least one assay site, the site comprising a pair of stimulating electrodes, a cell confinement cavity for confining at least one cell, and one or more sensor electrodes, wherein the cell confinement cavity and the stimulating electrodes are arranged so that, in use, each confined cell is exposable to a region of substantially uniform electrical field generated by the stimulating electrodes, and in which the region of substantially uniform electrical field is bounded at one side by the floor of the cell confinement cavity.

12. A device according to claim 11, in which in the region of substantially uniform electrical field the electrical field strength varies transversely to the electrical field lines by no more than 10%.

13. A device according to claim 11, in which the region of substantially uniform electrical field extends along and/or transversely to the direction of the electrical field lines for a distance at least 2 µm.

14. A device according to claim 11, in which the region of substantially uniform electrical field occupies a volume of at least 1 pL.

15. A device for performing cell assays, which device has at least one assay site, the site comprising a pair of stimulating electrodes, a cell confinement cavity for confining at least one cell, and one or more sensor electrodes, wherein the cell confinement cavity and the stimulating electrodes are arranged so that, in use, each confined cell is exposable to a region of substantially uniform electrical field generated by the stimulating electrodes, and in which the stimulating electrodes extend in the direction perpendicular to the floor of the cell confinement cavity at opposing sides of the cell confinement cavity.

16. A device according to claim 15, in which the stimulating electrodes extend in the direction perpendicular to the floor of the cell confinement cavity for a distance of at least 2 µm.

17. A device for performing cell assays, which device has at least one assay site, the site comprising a pair of stimulating electrodes, a cell confinement cavity for confining at least one cell, and one or more sensor electrodes, wherein the cell confinement cavity and the stimulating electrodes are arranged so that, in use, each confined cell is exposable to a region of substantially uniform electrical field generated by the stimulating electrodes, and in which the stimulating electrodes are formed by electroplating from solution.

18. A device for performing cell assays, which device has at least one assay site, the site comprising a pair of stimulating electrodes, a cell confinement cavity for confining at least one cell, and one or more sensor electrodes, wherein the cell confinement cavity and the stimulating electrodes are arranged so that, in use, each confined cell is exposable to a region of substantially uniform electrical field generated by the stimulating electrodes, and in which the stimulating electrodes are coated with a chargeable surface area enhancing agent.

* * * * *